US012780855B2

(12) United States Patent
Romero-Nieto et al.

(10) Patent No.: US 12,780,855 B2
(45) Date of Patent: Nov. 3, 2026

(54) PHOSPHAPHENALENE-GOLD(I) COMPLEXES AS CHEMOTHERAPEUTIC AGENTS AGAINST GLIOBLASTOMA

(71) Applicant: UNIVERSITY OF CASTILLA-LA-MANCHA, Ciudad Real (ES)

(72) Inventors: Carlos Romero-Nieto, Socuéllamos (ES); Saskia Rösch, Cologne (DE); Christel Herold-Mende, Bammental (DE); Valentina Fermi, Mannheim (DE)

(73) Assignee: UNIVERSITY OF CASTILLA-LA-MANCHA, Ciudad Real (ES)

( * ) Notice: Subject to any disclaimer, the term of this patent is extended or adjusted under 35 U.S.C. 154(b) by 472 days.

(21) Appl. No.: 18/249,008

(22) PCT Filed: Oct. 13, 2021

(86) PCT No.: PCT/EP2021/078277

§ 371 (c)(1),
(2) Date: Apr. 13, 2023

(87) PCT Pub. No.: WO2022/079085

PCT Pub. Date: Apr. 21, 2022

(65) Prior Publication Data

US 2023/0391808 A1 Dec. 7, 2023

(30) Foreign Application Priority Data

Oct. 13, 2020 (EP) .................................... 20201555

(51) Int. Cl.

| | |
|---|---|
| ***C07F 1/12*** | (2006.01) |
| ***A61K 31/555*** | (2006.01) |
| ***A61K 31/675*** | (2006.01) |
| ***A61P 35/00*** | (2006.01) |
| ***C07F 9/6578*** | (2006.01) |
| ***C07F 9/6584*** | (2006.01) |

(52) U.S. Cl.

CPC ............ *C07F 9/6584* (2013.01); *A61P 35/00* (2018.01); *C07F 9/6578* (2013.01)

(58) Field of Classification Search

CPC ........ C07F 1/12; C07F 9/6584; C07F 9/6578; A61K 31/555; A61K 31/675; A61P 35/00

See application file for complete search history.

(56) References Cited

U.S. PATENT DOCUMENTS 7,923,434 B2 4/2011 Scient

OTHER PUBLICATIONS

PCT International Search Report and Written Opinion for PCT/EP2021/078277, mailed Jan. 21, 2022 (10 pages).

Jortzik E et al: "Antiglioma activity of GoPI-sugar, a novel gold(I)-phosphole inhibitor: Chemical synthesis, mechanistic studies, and effectiveness in vivo", Biochimica Et Biophysica Acta (BBA)—Proteins & Proteomics, Elsevier, Netherlands, vol. 1844, No. 8, Jan. 16, 2014 (Jan. 16, 2014), pp. 1415-1426.

Philip Hindenberg et al:"A Guide for the Design of Functional Polyaromatic Organophosphorus Materials", Chemistry—A European Journal, vol. 23, No. 56, Oct. 9, 2017 (Oct. 9, 2017), pp. 13919-13928.

Carlos Romero-Nieto et al: "Paving the Way to Novel Phosphorus-Based Architectures: A Noncatalyzed Protocol to Access Six-Membered Heterocycles", Angewandte Chemie International Edition, vol. 54, No. 52, Nov. 9, 2015 (Nov. 9, 2015), pp. 15872-15875.

*Primary Examiner* — Bruck Kifle
(74) *Attorney, Agent, or Firm* — Snell & Wilmer LLP

(57) ABSTRACT

Glioblastoma is one of the most lethal brain tumors. Difficulties for the treatment of glioblastoma involve, among others, the sensitivity of the brain to drugs, the limited brain penetration of chemotherapeutic agents and the resistance of tumor cells to conventional therapies. Provided are specific phosphaphenalene-gold (I) complexes for use as a medicament, especially in the treatment of brain cancer such as glioblastoma, a pharmaceutical composition and a kit comprising such complex.

21 Claims, 4 Drawing Sheets

PHOSPHAPHENALENE-GOLD(I) COMPLEXES AS CHEMOTHERAPEUTIC AGENTS AGAINST GLIOBLASTOMA

CROSS REFERENCE TO RELATED APPLICATIONS

This application claims priority to PCT/EP2021/078277, filed on Oct. 13, 2021, which claims the benefit of European Application No. 20201555.8, filed on Oct. 13, 2020, the entire contents of which are incorporated by reference herein.

TECHNICAL FIELD

The present invention is directed to phosphaphenalene-gold (I) complexes for use as a medicament, especially in the treatment of brain cancer such as glioblastoma, a pharmaceutical composition and a kit comprising such complex and the use of such complex for inhibiting the activity of thioredoxin reductase (TrxR), in vitro/ex vivo.

BACKGROUND OF THE INVENTION

Glioblastoma (GBM) is the most common and malignant human brain tumor with a survival time of only about 15 months. Some key reasons are a rapid tumor cell proliferation, tumor heterogeneity, genetic instability, and a highly infiltrative growth. Especially, the latter requires a systemic treatment to target disseminated tumor cells that cannot be surgically removed. Thus, current treatment consists of surgery followed by a combined radio- and Temozolomide-based chemotherapy. However, 40%, 17.4%, and 5.6% one-, two-, and five-year survival rates, respectively, are still very poor, indicating a substantial resistance of at least a sub-population of tumor cells towards this type of treatment.

It has been hypothesized that this might be due to an immature, highly tumorigenic cell population endowed with stem cell-like properties such as self-renewal and a reduced sensitivity to chemotherapy, which seem to be responsible for tumor recurrence.

These findings underline an urgent need for the development of more effective therapeutic agents capable to eradicate all tumor cell populations and thus to prevent tumor regrowth.

Additional challenges for novel therapeutic drugs to overcome the resistance of brain tumor cells to current chemotherapy are the necessity to cross the blood-brain-barrier (BBB) and exert tumor-selective activity. In this regard, gold (I) complexes are promising compounds; they have the capacity to cross the BBB (Jortzik E. et al. "*Antiglioma activity of GoPI-sugar, a novel gold(I)-phosphole inhibitor: Chemical synthesis, mechanistic studies, and effectiveness in vivo*", Biochimica et Biophysica Acta (BBA)—Proteins and Proteomics 2014, 1844 (8), pages 1415-1426).

One of the most accepted hypotheses on the mode of action of gold complexes includes a specific inhibition of the thioredoxin reductase (TrxR); which is an enzyme involved in the cellular redox homeostasis and has been shown to be overexpressed in tumor cells (Gandin V. et al., "*Metal-and Semimetal-Containing Inhibitors of Thioredoxin Reductase as Anticancer Agents*", Molecules, 2015, 20(7), 12732-12756).

Gold (I) complexes have an enormous potential for the selective inhibition of TrxR; they have the ability to specifically interact with the SH/Se centers of the thioredoxin enzyme, inhibiting its activity and ultimately leading to cell apoptosis (Zou T. et al., "*Chemical biology of anticancer gold(III) and gold(I) complexes*", Chem. Soc. Rev. 2015, 44, 8786-8801).

Nevertheless, even though the use of gold complexes in medicine, chrysotherapy, dates from the ancient Egyptian times, clinical applications of the latter gold complexes are nowadays rather low. Several authors have attributed this fact to "the poor stability" and "solubility" of the tested compounds (Nobili S. et al., "*Gold compounds as anticancer agents: chemistry, cellular pharmacology, and preclinical studies*", Med. Res. Rev. 2010, 30, 550-580; and Gandin V. et al., cited above).

Currently, the most investigated gold complexes for cancer treatment are Auranofin and derivatives. Their general structure consists of a linear molecule with a tri-substituted phosphine ligand (Fragment A) attached to the Au atom, which in turn bonds an additional anionic ligand (Fragment B).

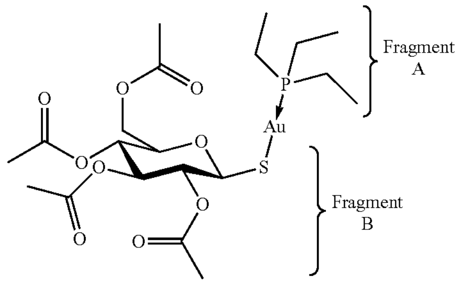

Auranofin

Mechanistic investigations revealed that both ligands modulate the anti-tumor activity of gold complexes (Gandin V. et al., cited above). First, Fragments A and B must provide enough solubility in aqueous media to ensure the bioactivity of the complex. Then, Fragment B must be labile enough to permit the initial coupling of gold to specific carrier enzymes. In turn, the electronic properties of Fragment A play a crucial role; they must furnish a robust stability to the species that actively inhibits the TrxR (i.e. the $R_3P$—$Au^+$) to attain the target. Weak P—Au bonds lead to hydrolysis, irreversible oxidation of the phosphorus and the formation of inactive colloidal gold. In addition, the lipophilicity and steric hindrance of Fragment A are fundamental for the gold moiety to penetrate the cells (Zou T. et al., cited above). Thus, enhancing the bioactivity of molecular systems is a hurdle task since it is the result of a variety of synergistic characteristics.

The most employed moieties for Fragment A are homo-trisubstituted phosphines. Phosphorous containing moieties, especially, heterocycles for Fragment A have rarely been tested for cancer therapy. Only complexes based on five-membered heterocycles, the 2,5-diarylphospholes, have been used to date.

Deponte M. et al., "*Mechanistic studies on a novel, highly potent gold-phosphole inhibitor of human glutathione reductase*", J. Biol. Chem. 2005, 280, 20628-20637, reported the chloro gold complex "[1-phenyl-2,5-di(2-pyridyl)phosphole]AuCl" as a novel gold-phosphole inhibitor (GoPI), being able to inhibit human glutathione reductase, and further showed that GoPI inhibits proliferation of glioblastoma cell lines with $IC_{50}$ values for NCH82 and NCH89 of 12.5±0.8 μM and 10.8±0.8 μM, respectively.

The effects of phosphole-containing gold and platinum complexes on human glutathione reductase (hGR) and thioredoxin reductase (hTrxR) as well the growth inhibitory action on tumor cells were described by Urig S. et al., "*Undressing of Phosphine Gold*(1) *Complexes as Irreversible Inhibitors of Human Disulfide Reductases*", Angew. Chem. Int. Ed., 2006, 45, pages 1881-1886. The antiproliferative effects of five different phosphole-containing complexes ($IC_{50}$) on NCH82 and NCH89 were reported as 7.2 μM-81.8 μM and 10.8 μM-87.4 μM, respectively.

Further, Viry E. et al., "*A sugar-modified phosphole gold complex with antiproliferative properties acting as a thioredoxin reductase inhibitor in MCF-*7 *cells*", ChemMedChem 2008, 3, 1667-1670, evaluated different compounds for their cytotoxic activities against the human breast cancer MCF-7 cell line, inter alia phosphole-containing gold and platinum complexes.

Jortzik E. et al. (cited above) reported antitumor properties of the gold(I) complex 1-phenyl-bis(2-pyridyl)phosphole gold chloride thio-β-d-glucose tetraacetate (GoPI-sugar), which exhibits antiproliferative effects on human (NCH82, NCH89) and rat (C6) glioma cell lines, and that GoPI-sugar inhibits thioredoxin reductase ($IC_{50}$ 4.3 nM) and human glutathione reductase ($IC_{50}$ 88.5 nM).

The cytotoxic activity of different phosphole gold complexes is also disclosed in U.S. Pat. No. 7,923,434 B2.

However, it is reported in the prior art that some of these phosphole gold complexes are unstable in aqueous solutions (Viry E. et al., cited above).

Departing from the prior art, it is thus an object of the present invention to provide compounds for use as a medicament, especially in the treatment of brain cancer such as glioblastoma, having improved stability, being capable to cross the blood-brain barrier and inhibit tumor cell proliferation as well as sensitize tumor cells to undergo apoptosis. A further object is to provide pharmaceutical composition and a kit comprising such compounds.

SUMMARY OF THE INVENTION

These objects have been solved with the compounds for use according to claim 1, the pharmaceutical composition according to claim 10 and the kit according to claim 14. Subject of the present invention is further the in vitrolex vivo use of these compounds for inhibiting the activity of thioredoxin reductase (TrxR) according to claim 15.

According to the present invention is provided the compound of Formula (A) for use as a medicament, (A)

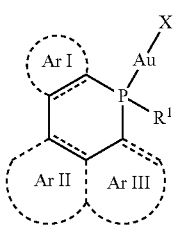

wherein

Ar I represents a monocyclic aromatic moiety selected from the group consisting of phenyl, pyridine, pyrrole, N-protected pyrrole, furan, thiophene and seven-membered aromatic monocycles, or represents a bicyclic aromatic moiety selected from the group consisting of naphthalene, indole and benzothiophene, wherein Ar I may be substituted by one or more substituents selected from the group consisting of a halogen atom, preferably wherein the halogen atom is selected from Cl, Br, I and F, a five- or six-membered aromatic heterocycle containing N, S or O, a $C_{1-6}$ aliphatic group and a $C_{3-6}$ cycloaliphatic group, wherein the $C_{1-6}$ aliphatic group and/or the $C_{3-6}$ cycloaliphatic group may additionally contain one or more heteroatoms selected from N, S and O, Ar II and Ar III each independently represent a benzene group, a pyridine group, a pyrrole group, a N-protected pyrrole group or a thiophene group;

$R^1$ represents an aromatic group, a hydroxy group, a $C_1$-$C_6$ alkyl group or a $C_1$-$C_6$ alkoxy group, preferably a phenyl group; and X is selected from the group consisting of sugars, albumins, halogen atoms, $CH_3$, $NO_3$, CN, and $SR^3$, wherein $R^3$ is selected from the group consisting of 2,3,4,6-tetra-O-acetyl-β-D-glucopyranosyl, β-D-glucopyranosyl, 2,3,4,6-tetramesyl-β-D-glucopyranosyl, 2,3,4,6-tetra-O-acetyl-α-D-glucopyranosyl, 2,3,4,6-tetra-O-acetyl-β-D-galactopyranosyl, hepto-O-acetyl-β-maltosyl, 1,2-O-isopropylidene-5-α-D-xylofuranosyl, $C_1$-$C_8$ alkyl, $CH(CO_2H)CH_2CO_2H$, 2-morpholinoethyl, 2'-ethyl-1-β-D-glucopyranosyl, 2'-ethyl-1-thio-β-D-glucopyranosyl, glutathionyl hydrochloride, CN, $C(NH_2)_2{\cdot}HCl$, $C(NH_2)NHNH_2$, phenyl, 1-aminophenyl, 2-pyridyl, 6-methyl-2-pyridyl, 4-pyridyl, thiazoline-2-yl, 4,5-dihydrothiazol-2-yl, 1H-benzimidazol-2-yl, benzoxazol-2-yl, benzothiazol-2-yl, $(CH_2CH_2OH)_2NO_3^-$, pyrimidin-2-yl, 4-methylpyrimidin-2-yl, 4,6-dimethylpyrimidin-2-yl, 1,2-dihydropyridin-2-yl, 1,2-dihydropyrimidin-2-yl, 9H-purin-6-yl, 2-amino-9H-purin-6-yl, and $(NH_2)_2C{=}$.

The compounds according to the present invention are based on fused six-membered phosphorous heterocycles being derivatives of phosphaphenalene. Until now, six-membered phosphorus derivatives have not been investigated for cancer therapy. The compounds according to the present invention further possess structural and electronic properties that strongly differ from phosphines and phospholes known so far as possible chemotherapeutic agents.

The preparation of chloro gold(I) complexes based on a phosphaphenalene system was described in Romero-Nieto C. et al., "*Paving the Way to Novel Phosphorus-Based Architectures: A Noncatalyzed Protocol to Access Six-Membered Heterocycles*", Angew. Chem. Int. Ed. 2015, 54(52), 15872-15875.

It has now been found that the compounds according to the present invention not only showed an unexpectedly high stability in dimethylsulfoxide/$H_2O$ solutions but also cytotoxic effects.

According to the present invention, it is preferred that in the above Formula (A) Ar II and Ar III together represent a naphthalene group, an indole group, a N-protected indole group, a quinoline group, a N-protected quinoline group or a benzothiophene group.

According to a preferred embodiment of the present invention, Ar II and Ar III together represent a naphthalene group.

It is further preferred, that Ar I is a benzene group, a naphthalene group, a thiophene group, a furan group, a pyrrole group, a benzothiophene group, or a pyridine group, wherein Ar I may be substituted by one or more substituents selected from the group consisting of a halogen atom, preferably wherein the halogen atom is selected from Cl, Br, I and F, a five- or six-membered aromatic heterocycle containing N, S or O, a $C_{1-6}$ aliphatic group and a $C_{3-6}$ cycloaliphatic group, wherein the $C_{1-6}$ aliphatic group and/or the $C_{3-6}$ cycloaliphatic group may additionally contain one or more heteroatoms selected from N, S and O.

According to a preferred embodiment, Ar I is not substituted. According to another preferred embodiment, Ar I is substituted by one or two, more preferably one, substituent selected from the group mentioned above.

In the above Formula (A), Ar I is preferably selected from the group consisting of phenyl, pyridine, pyrrole, N-protected pyrrole, furan, thiophene. According to a preferred embodiment, Ar I is a thiophene group, more preferably an unsubstituted thiophene group.

According to a preferred embodiment Ar I is a pyrrole group, more preferably Ar I is an N-substituted pyrrole group with a methyl group or a phenylsulfonyl group as substituent on the N atom, particularly preferably with a methyl group as substituent on the N atom.

According to a preferred embodiment X in the above Formula (A) is selected from the group consisting of Cl, xanthate, thiocyanide, and 3,4,5-triacetyloxy-6-(acetyloxy-methyl)oxane-2-thiolate. It is further preferred that X is xanthate or 3,4,5-triacetyloxy-6-(acetyloxymethyl)oxane-2-thiolate, more preferably X is 3,4,5-triacetyloxy-6-(acety-loxy-methyl)oxane-2-thiolate.

According to one particular embodiment of the present invention, Ar I is an N-substituted pyrrole group with a methyl group as substituent on the N atom, Ar II and Ar III together represent a naphthalene group, $R^1$ is a phenyl group, and X is 3,4,5-triacetyloxy-6-(acetyloxymethyl) oxane-2-thiolate.

According to one embodiment of the present invention, the compound of the present invention is Compound 1. According to another embodiment of the present invention, the compound of the present invention is Compound 2. According to another embodiment of the present invention, the compound of the present invention is Compound 3. According to another embodiment of the present invention, the compound of the present invention is Compound 4.

According to another embodiment of the present invention, the compound of the present invention is Compound 5. According to another embodiment of the present invention, the compound of the present invention is Compound 6. According to another embodiment of the present invention, the compound of the present invention is Compound 7. According to another embodiment of the present invention, the compound of the present invention is Compound 8. It is to be understood that Compounds 5 to 8 form part of the invention as compounds as such, irrespective of their specific uses provided herein.

The protecting groups of Ar I, Ar II and Ar III, i.e. for the N-protected pyrrole group, N-protected indole group and/or N-protected quinoline group, are preferably selected from $Si(CH_3)_3$, $SO_2Ph$ and sugars. However, other suitable protecting groups as commonly known in the art can also be used.

With respect to the position of the heteroatom(s) in the aforementioned cyclic groups containing heteroatoms, the compounds according to the present invention comprise all possible structural isomers.

According to one embodiment of the present invention, the present invention provides a compound of Formula (B),

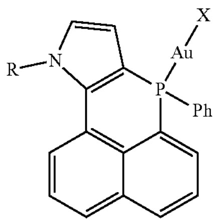

(B)

wherein R is methyl or $SO_2Ph$, and wherein X is chloride or 3,4,5-triacetyloxy-6-(acetyloxymethyl)oxane-2-thiolate, preferably wherein R is methyl and wherein X is 3,4,5-triacetyloxy-6-(acetyloxymethyl)oxane-2-thiolate. According to one embodiment of the present invention, said compound is provided for use as a medicament.

According to a preferred embodiment, the compounds according to the present invention are for use in the treatment of cancer.

According to a further preferred embodiment, the compounds according to the present invention are for use in the treatment of brain cancer, preferably for use in the treatment of glioblastoma.

Subject matter of the present invention is further a pharmaceutical composition comprising a compound according to the present invention and at least one pharmaceutically acceptable excipient. The pharmaceutical composition is preferably characterized by being administered intravenously.

In addition, it is preferred that in the pharmaceutical composition according to the present invention the compound is dissolved in an aqueous solution comprising DMSO, preferably wherein the compound is dissolved in a mixture of water and DMSO, more preferably in water comprising 5 to 20 vol % DMSO. Preferably, the pharmaceutical composition as described herein is for use as a medicament.

According to one preferred embodiment, the pharmaceutical composition is for use in the treatment of cancer, more preferably for use in the treatment of brain cancer, even more preferably for use in the treatment of glioblastomas, brain metastases, meningiomas, IDH-mutant gliomas, or head and neck cancer, particularly preferably for use in the treatment of glioblastoma.

The present invention is further directed to a kit comprising at least a compound according to the present invention as described above and a container.

Subject matter of the present invention is further the use of the compound according to the present invention as described above for inhibiting the activity of thioredoxin reductase (TrxR), wherein the compound is used in vitro/ex vivo.

One aspect of the invention further relates to a method of treatment of a subject, wherein the compound as described herein, the pharmaceutical composition as described herein, or the kit as described herein is used as part of said treatment.

The present invention will become more apparent from the following detailed description of the present invention when taken in conjunction with the accompanying drawings.

DESCRIPTION OF FIGURES

FIG. 3A depicts the flow cytometry analysis of NCH89 untreated cells and upon exposure to 1 μM, 2 μM, and 10 μM of compound 4 for 24 hours; FIG. 3B is a stack chart showing the relative percentage of apoptotic and necrotic cells of conventional glioblastoma cell lines NCH82 and NCH89; FIG. 3C is a stack chart showing the relative percentage of apoptotic and necrotic cells of glioma stem cell lines NCH421k, NCH644, and NCH660h.

DETAILED DESCRIPTION OF THE INVENTION

Figure 1:
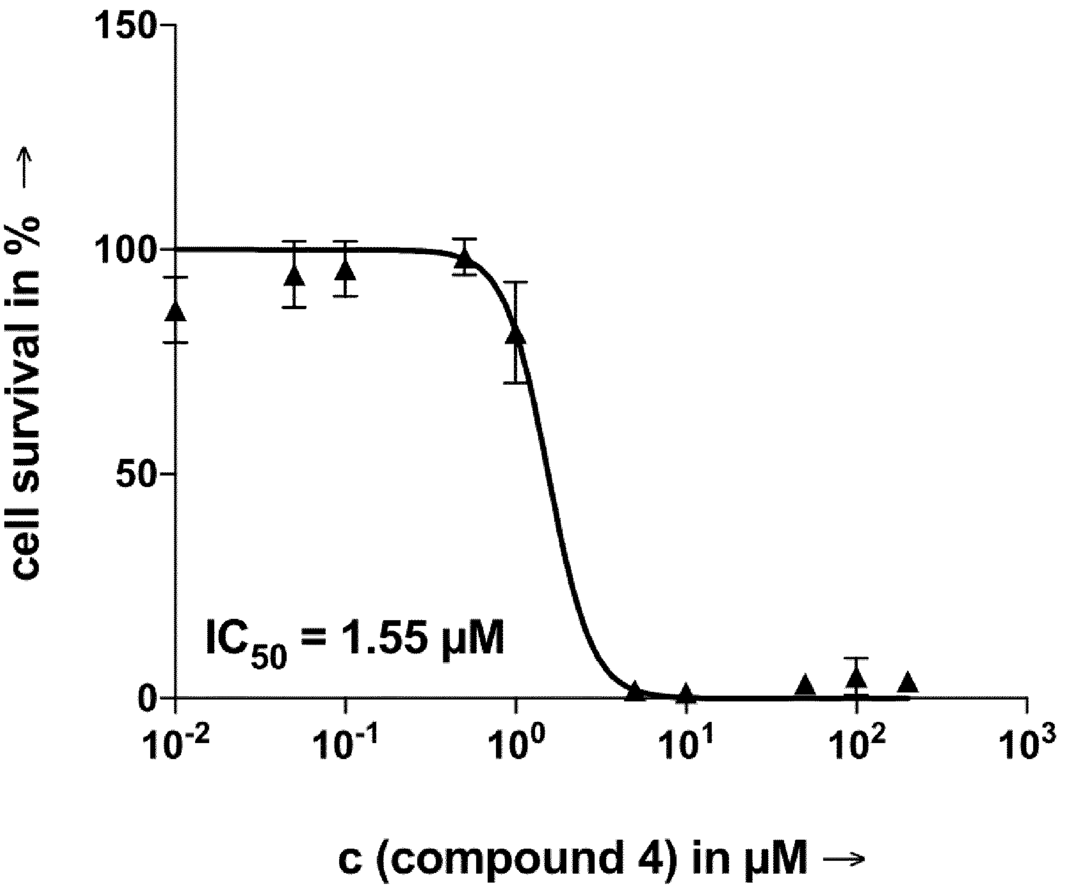
FIG. 1 shows a dose-response curve for NCH82 cells obtained from one of three biological replicates of Compound 4 at 48 hours. In this replicate, Compound 4 inhibited NCH82 tumor cell growth with an $IC_{50}$ of 1.55 μM.

During evaluation of the compounds of the present invention, the present inventors recognized that gold-phosphaphenalene derivatives were surprisingly soluble and highly stable in dimethylsulfoxide/$H_2O$ solutions over weeks.

Even the chloro derivative (Compound 1 shown below) showed such high stability, in contrast to the analogue 2,5-diarylphosphole gold complex which was reported as being unstable in aqueous solutions (Viry E. et al., cited above).

In a first step, the electronic characteristics of the compounds of the present invention were examined by comparing the above mentioned phosphaphenalene chloro derivative (Compound 1), wherein Fragment B is Cl, represented by the following Formula (I):

Compound 1

(I)

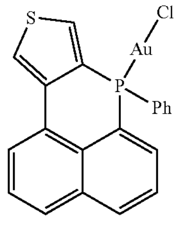

X = Cl with a series of different chloro derivatives including the [1-phenyl-2,5-di(2-pyridyl)-phosphole]AuCl, triphenylphosphine-AuCl ($Ph_3PAuCl$) and triethylphosphine-AuCl ($Et_3PAuCl$).

All of these complexes contain distinct phosphorus ligands that were reported as Fragment A for the synthesis of Auranofin-like structures. [1-phenyl-2,5-di(2-pyridyl)-phosphole]AuCl was reported as a novel gold-phosphole inhibitor (GoPI) by Deponte M. et al., cited above.

As a reflection of the distinct electronic properties of the latter phosphorus ligands, their $^{31}P$-NMR strongly differed within the AuCl complex series. While the $^{31}P$ signals of [1-phenyl-2,5-di(2-pyridyl)phosphole]AuCl, $Ph_3PAuCl$ and $Et_3PAuCl$ are in the range of 32-40 ppm, Compound 1 presents a singlet at 2.6 ppm (see Table 1). In line with the $^{31}P$-NMR, although the differences are rather limited, the P—Au bond distance for Compound 1 (2.225 Å) is smaller than for the other gold complexes, which are in the range of 2.230-2.231 Å (Table 1). The latter indicate both a stronger electron-donating ability of the phosphaphenalene and thus a stronger P—Au bond for Compound 1.

The steric demand of the phosphorus-based ligands is an important feature, since it relates not only to their stability but it also plays an important role in the penetration of cell membranes. Thus, to provide insight into the steric hindrance of these compounds, the percent buried volume (V %) was calculated and the electronic density of the phosphorus ligands that penetrates into the coordination sphere of the gold atom was mapped.

The higher the value V %, the more shielded is the gold atom. Thus, the V % value of the phosphaphenalene ligand in Compound 1 is comparable to $Ph_3P$ (30.7%). The lowest value (27.9%) is found for triethylphosphine, while the highest belongs to the 2,5-di(2-pyridyl)phosphole derivative (32.8%), probably due to the presence of pyridyl substituents in the gold coordination sphere.

After having corroborated the contrasting properties of the phosphaphenalene ligand versus phospholes and phosphines, the effect of Fragments B was analyzed. For this, three further compounds, Compounds 2, 3 and 4 as represented by the following Formulas (II), (III) and (IV), have been investigated.

Compound 2

(II)

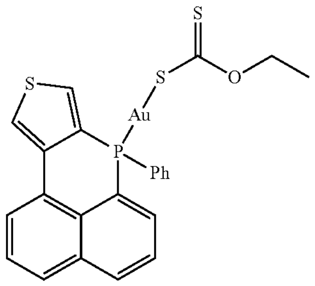

X = xanthate

Compound 3

(III)

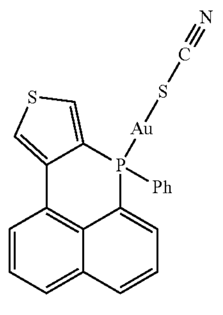

X = thiocyanide

-continued

Compound 4

(IV)

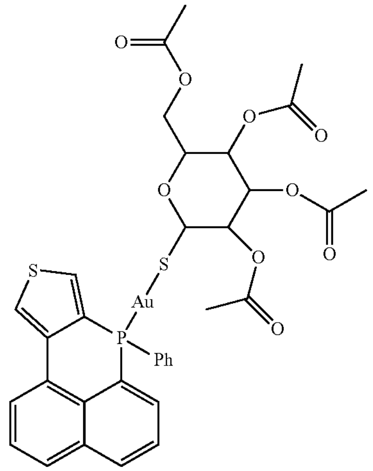

X = 3,4,5-Triacetyloxy-6-(acetyloxymethyl) oxane-2-thiolate

Importantly, all compounds 1-4 readily dissolved in DMSO/$H_2O$ mixtures 1:9. Compound 1 was the least soluble and started to precipitate at concentrations higher than 0.1 M. On the other hand, Compound 4 was soluble in the largest variety of solvents: i.e., methanol, ethanol, DCM, $CHCl_3$, $Et_2O$ and acetone, and insoluble in pentane and hexane.

Regarding the $^{31}$P-NMR features, by changing Fragment B, the signal was shifted from 2.56 ppm for Compound 1 to 6.65, 7.1 and 8.17 ppm for Compounds 2, 3, and 4, respectively (see Table 1). Again, this is in stark contrast with the phosphole and phosphine analogues, whose $^{31}$P-NMR signals are found at over 30 ppm. To obtain further details on the structural properties of Compounds 1-4, X-ray analyses were carried out.

To that end, Compounds 2 and 3 were successfully crystallized and their characteristics were compared with the parent compound 1 (Table 1). Unfortunately, attempts to crystallize Compound 4 with a pool of techniques and solvents over months were unsuccessful.

Within the series of Compounds 1-3, the Au—P bond length are slightly elongated from 2.225 Å for Compound 1 to 2.243 Å and 2.25 Å for Compounds 2 and 3, respectively. The Au-Fragment B bond distance follows the same trend, from 2.293 Å for Compound 1 to 2.326 Å and 2.332 Å for Compounds 2 and 3.

TABLE 1

$^{31}$P-NMR, P—Au distances and percent buried volume V %

| | $^{31}$P-NMR (ppm) | P—Au distance (Å) | V % |
|---|---|---|---|
| Compound 1 - Formula (I) | 2.56 | 2.225 | 30 |
| [1-phenyl-2,5-di(2-pyridyl)phosphole]AuCl | 39.9 | 2.230 | 32.8 |
| Triphenylphosphine-AuCl ($Ph_3PAuCl$) | 33.8 | 2.231 | 30.7 |
| Triethylphosphine-AuCl ($Et_3PAuCl$) | 32.32 | 2.231 | 27.9 |
| Compound 2 - Formula (II) | 6.65 | 2.243 | — |
| Compound 3 - Formula (III) | 7.10 | 2.25 | — |
| Compound 4 - Formula (IV) | 8.17 | — | — |

Experiments carried out to verify the stability of complexes 1-4 by monitoring $^1$H-NMR for 72 hours (which exceeds the common measurement time for bio-assays) revealed no signs of decomposition.

After having analyzed the features of Compounds 1-4, in vitro experiments were carried out. First, the most effective Fragment B of the phosphaphenalene-gold (I) complexes 1-4 was systematically investigated for the inhibition of glioma cell proliferation by crystal violet proliferation assay. To this end, GBM cell lines NCH82 and NCH89 were incubated for 48 hours with increasing concentrations of Compounds 1, 2, 3, and 4, respectively.

All derivatives revealed to be active for the inhibition of glioma cell proliferation (see Table 2). While compounds 1-3 showed mean $IC_{50}$ values in the range of 8.21±0.52 μM to 11.4±0.11 μM, and 15.1±0.71 μM to 18.1±1.04 μM for NCH82 and NCH89, respectively, the strongest antiproliferative effects were observed for the thio-sugar containing Compound 4 with mean $IC_{50}$ values of 1.44±0.16 μM and 2.9±0.41 μM for GBM cell lines NCH82 and NCH89, respectively.

FIG. 1 exemplarily shows one of three biological replicates of compound 4 applied on NCH82.

To further corroborate the activity of the latter complex, additional primary glioblastoma cell lines NCH210 and NCH125 were treated with Compound 4, obtaining comparable and even better mean $IC_{50}$ values; i.e. 2.79±0.07 μM and 0.78±0.04 μM, respectively (Table 2).

TABLE 2

Antiproliferative effects of compounds 1-4 upon treatment of four glioblastoma (GBM) cell lines (expressed as mean $IC_{50}$ values (μM) of three biological replicates ± standard deviation).

| GBM cell line | Compound 1 | Compound 2 | Compound 3 | Compound 4 |
|---|---|---|---|---|
| NCH82 | 11.4 ± 0.11 | 11.17 ± 0.35 | 8.21 ± 0.52 | 1.44 ± 0.16 |
| NCH89 | 17.3 ± 1.02 | 18.1 ± 1.04 | 15.1 ± 0.71 | 2.9 ± 0.41 |
| NCH210 | n.d. | n.d. | n.d. | 2.79 ± 0.07 |
| NCH125 | n.d. | n.d. | n.d. | 0.78 ± 0.04 |

n.d. = not determined

Based on the assumption that most drug-based therapies might fail due to therapy-resistant glioblastoma stem-like cells (GSCs), the inventors further investigated the possibility to target well-characterized GSC lines such as NCH421k, NCH644, and NCH660h. These cell lines were described by Campos B. et al., "*Differentiation therapy exerts antitumor effects on stem-like glioma cells*", Clin Cancer Res. 2010 May pages 2715-28.

To that end, in view of its antiproliferative properties, compound 4 was employed on GSCs growing as floating neurospheres using the CellTiterGlow® assay. As a result, the treatment of GSCs revealed remarkable mean $IC_{50}$ values of 6.95±1.95 μM, 6.60±1.98 μM, and 2.66±0.58 μM for NCH421k, NCH644, and NCH660h, respectively. Slightly higher $IC_{50}$ values for this specific type of cells might be caused by their profound self-renewal ability and reduced drug sensitivity; although the latter $IC_{50}$ values are still in a similar range as found for the conventional GBM cells.

Besides an increased tumor cell proliferation, a highly invasive cell growth drives malignancy of GBM. To obtain a more complete picture of the anti-cancer action of the compounds according to the invention, the effects of compound 4 on GBM cell invasion were investigated using a conventional wound-healing assay with NCH82, NCH89, NCH125, and NCH210 cells.

Application of compound 4 in different concentrations resulted in a significantly decreased wound closure compared to untreated control cells only when employing at least the corresponding $IC_{50}$ concentrations; the same was not observed at lower concentrations of compound 4.

The wound closure was not significantly affected at concentrations $c(IC_{50})/2$ and $c(IC_{50})/10$. Nevertheless, the short observation time of 24 hours, which only allows for a limited tumor cell proliferation to occur still supports that the mode of action of compound 4 might include an additional anti-migratory component at $IC_{50}$ values, besides its marked anti-proliferative properties.

Figure 2:
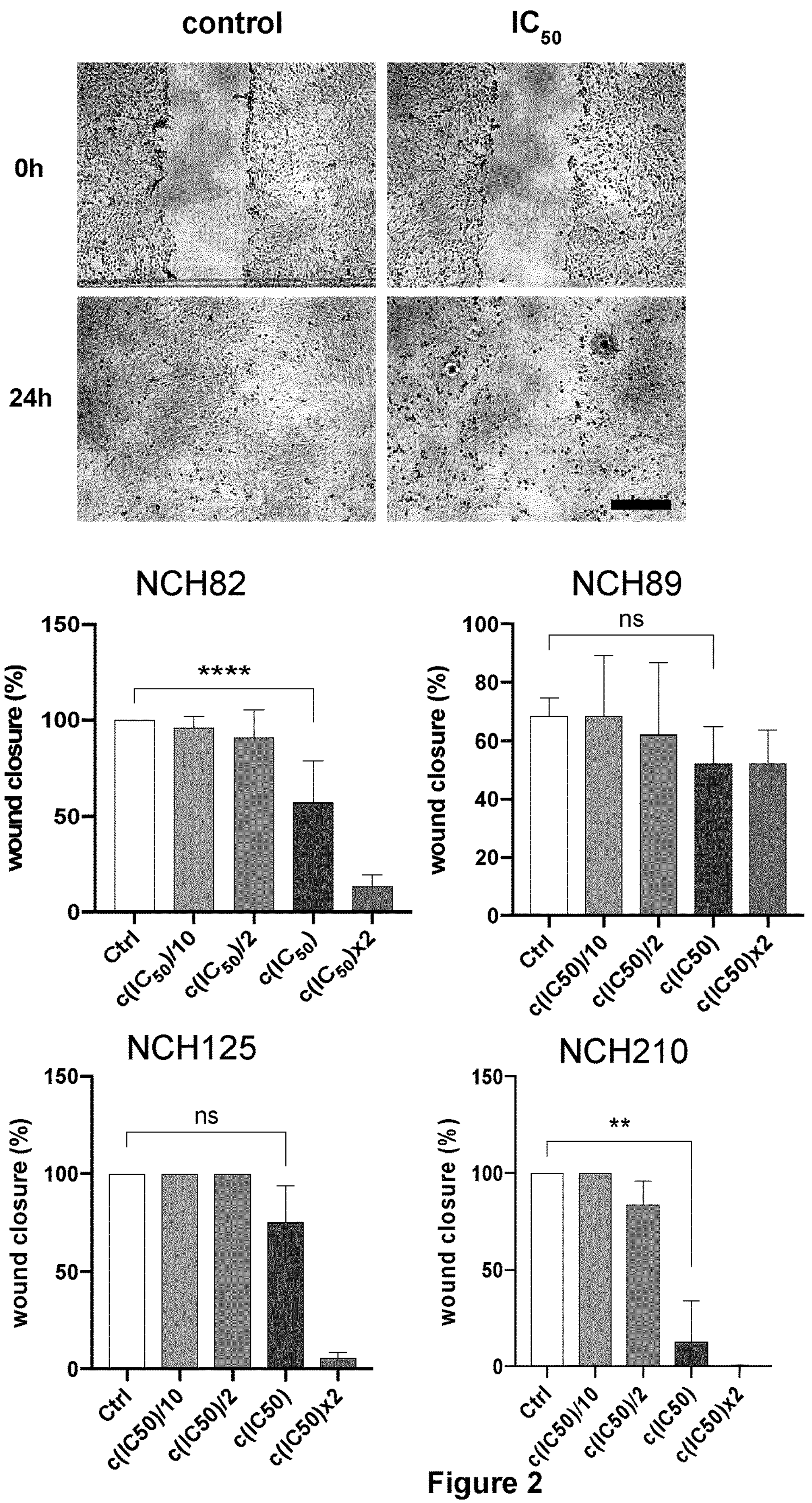
FIG. 2 shows the effects of Compound 4 on NCH82, NCH89, NCH125, and NCH210 tumor cell migration using the wound-healing assay.

The results of the wound-healing assay are depicted in FIG. 2. The wound-healing assay was carried out by scraping GBM cell monolayers with a pipet tip and treating it with concentrations of $c(IC_{50})/10$, $c(IC_{50})/2$, $c(IC_{50})$, and $c(IC_{50})\times 2$ of Compound 4 for 24 hours. The cells were imaged at 0 hours (t0) and at 24 hours (t1) after introducing the scrape. Cell migration was assessed by measuring cell-free areas at t0 and their reduction at t1.

In the upper left corner of FIG. 2 are photographs of NCH82 p85 tumor cells without (control) any treatment and treated with $c(IC_{50})$ of Compound 4, at incubation times 0 and 24 hours. The bar charts in FIG. 2 show data for each individual cell line represented as mean±standard deviation of three biological replicates.

Figure 3:
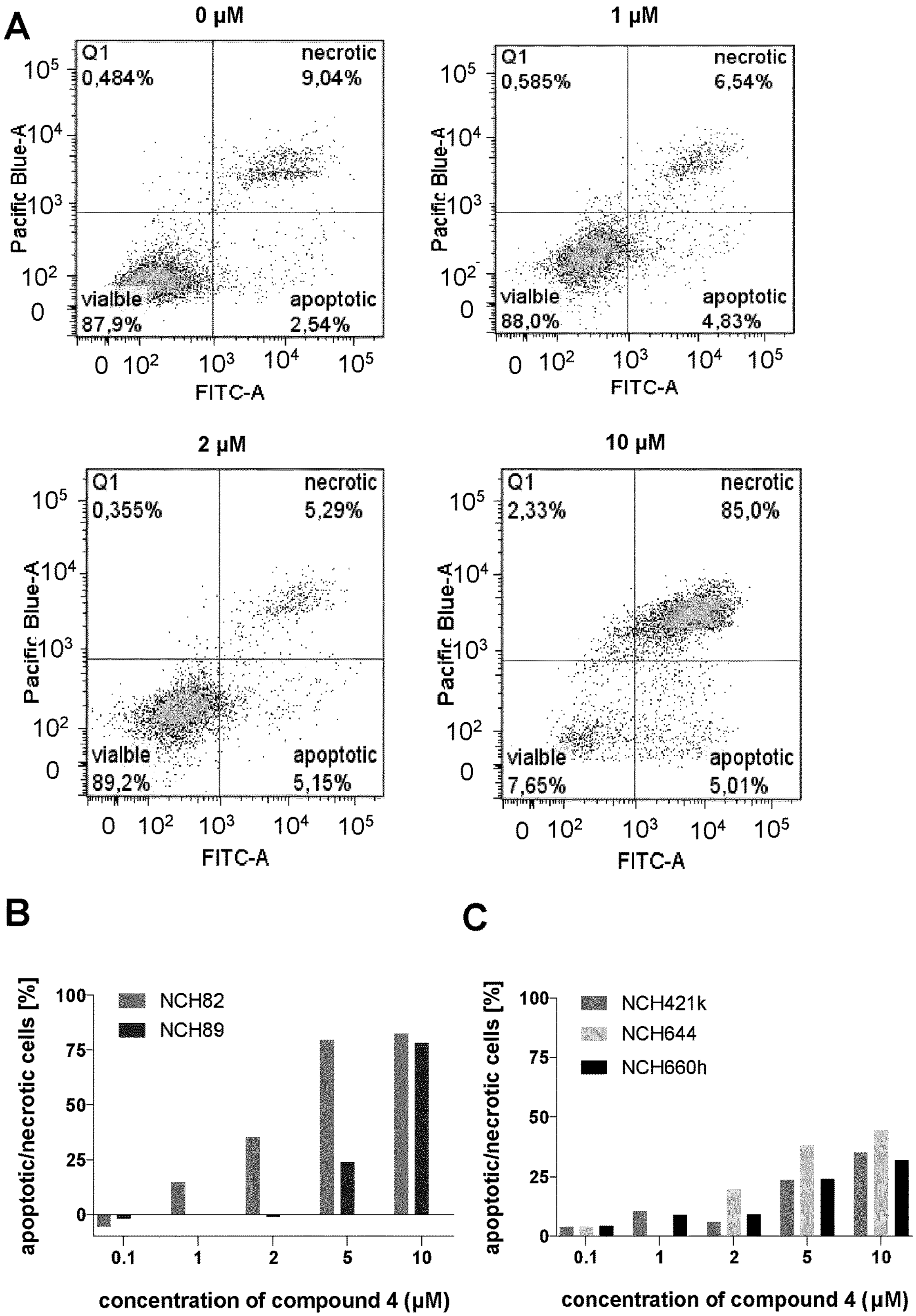
FIG. 3 shows the number of apoptotic/necrotic cells increasing with increasing concentrations of Compound 4.

It was further analyzed whether Compound 4 could sensitize GBM cells (NCH82 and NCH89) and GSCs (NCH421k, NCH644, and NCH660h) to apoptosis. The increase of apoptotic/necrotic cells with increasing concentrations of Compound 4 is illustrated in FIG. 3. FIG. 3A depicts flow cytometry analysis of NCH89 untreated cells and upon exposure to 1 μM, 2 μM, and 10 μM of compound 4 for 24 hours revealing a dose-dependent increase of apoptotic/necrotic cells.

FIG. 3B is a stack chart showing the relative percentage of apoptotic and necrotic cells of the conventional glioblastoma cell lines NCH82 and NCH89, and FIG. 3C is a stack chart showing the relative percentage of apoptotic and necrotic cells of glioma stem cell lines NCH421k, NCH644, and NCH660h.

Thus, after a 48 hour-incubation period with different concentrations of Compound 4, the conventional GBM cells and GSCs were analyzed by flow cytometry. Annexin V and propidium iodide (PI) were used as indicators for apoptosis/necrosis. In line with the obtained $IC_{50}$ values listed in Table 2, NCH82 cells appeared to be the most sensitive GBM cell line.

Already a drug concentration of 2 μM induced apoptosis in a high percentage of cells (FIG. 3B). In contrast, NCH89 cells were more resistant to programmed cell death; at a concentration of 2 μM of compound 4 we observed no cell death (FIG. 3B). For the analyzed GSCs (FIG. 3C) induction of apoptosis could be demonstrated but to a lesser extent.

It could be shown that he compounds as defined in claim 1, i.e. gold (I) complexes based on six-membered phosphorus heterocycles, have an outstanding potential for the development of novel chemotherapeutic agents against not only conventional glioblastoma cells but, importantly, also against glioblastoma stem-like cells.

This is the result of systematical assessments of the cytotoxic effect of four different phosphaphenalene-gold (I) derivatives, wherein the best results were found for the thio-sugar derivative, i.e. Compound 4. In particular, Compound 4 showed a significant suppression of cell proliferation for both conventional GBM cells and GSCs.

Moreover, it was shown that Compound 4 exhibits anti-migratory effects on glioblastoma cells and sensitizes conventional GBM cells and GSCs cells to apoptosis. The compounds according to the present invention provide high stability, satisfying solubility in aqueous media and provide a synthetic versatility to meet possible further requirements.

Departing from the encouraging findings obtained with the aforementioned Compounds 1 to 4, the inventors set out to develop further specific improved phosphaphenalene-gold(I)complexes demonstrating the excellent spectroscopic properties, stability and, most importantly, bioactivity of the compounds claimed herein.

In this regard, Compound 5 was tested which includes a pyrrole moiety fused with a phosphaphenalene core coordinated to an AuCl fragment as represented by the following Formula (V):

Compound 5

(V)

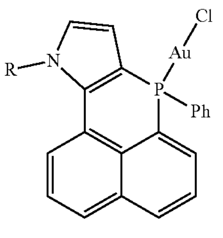

R = Me

Pyrrole-containing phosphaphenalenes are stable and have demonstrated outstanding optoelectronic properties in the context of material science; they possess fluorescence quantum yields up to 80% and have been employed in photoelectrochemical cells, organic light-emitting diodes and electrofluorochromic devices. Based on these properties, they could provide the additional advantage of drugs having significant spectroscopic properties, which are of particular value for mechanistic investigations in vivo.

Compound 5 was furthermore transformed into Compound 6, an analog compound to Compound 2 (see above), by replacing the chloride atom in Compound 5 with the 3,4,5-triacetyloxy-6-(acetyloxymethyl)oxane-2-thiolate in Compound 6 as shown in Formula (VI) (also referenced herein as Formula (B)) below:

Compound 6

(VI)

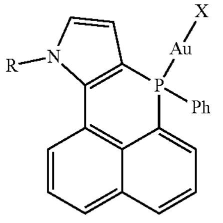

R = Me;
X = 3,4,5-Triacetyloxy-6-(acetyloxymethyl)oxane-2-thiolate

To analyze the impact of additional structural modifications on the bioactivity, the methyl substituent of the pyrrole was replaced by a bulkier substituent; i.e. a phenylsulfonyl. This led to Compound 7 carrying a chloride atom and the corresponding derivative Compound 8 with a 3,4,5-triacetyloxy-6-(acetyloxymethyl)oxane-2-thiolate moiety, as represented by Formulas (VII) and (VIII) below, respectively.

Compound 7

(VII)

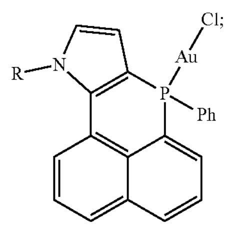

R = $SO_2Ph$

Compound 8

(VIII)

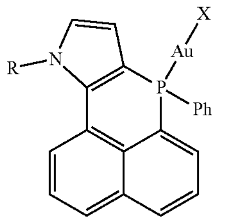

R = $SO_2Ph$;
X = 3,4,5-Triacetyloxy-6-(acetyloxymethyl)oxane-2-thiolate

The structural modifications led to changes into the molecules' electronic distribution; these are reflected in the $^1$H-NMR (data not shown). The substitution of the Cl atom of Compound 5 by the sugar derivative 3,4,5-triacetyloxy-6-(acetyloxymethyl)oxane-2-thiolate to yield Compound 6 only induced slight changes.

However, the N-substituents had a major impact. Introducing a phenylsulfonyl group at the nitrogen of the pyrrole-fused phosphaphenalene led to a dramatic deshielding of specific protons of the pyrrole fragment and of the naphthalene.

In turn, in comparison to the chloride derivatives Compound 1 and Compound 5, Compound 7 displays structural results stemming from the electron-withdrawing effect of the phenylsulfonyl group. On the other hand, all sugar derivatives Compound 4, Compound 6 and Compound 8 present distinctly deshielded $^{31}$P-NMR at 8.2, 9.1 and 9.5 ppm. These values are significantly lower than those observed for previously reported bio-active phosphole- and phosphine-based gold complexes which range between 32 and 47 ppm.

In order to investigate the role of the fused phosphaphenalene ring in the bio-activity of the drug, the ability of Compound 5 to inhibit cell proliferation in the glioblastoma cell lines NCH82, NCH89 and NCH149 was examined. For this purpose, cells were incubated with increasing concentrations of Compound 5 and cell proliferation was evaluated by crystal violet assay.

Compound 5 showed antiproliferative effects in all three cell lines. The mean $IC_{50}$ values for cell lines NCH82, NCH89 and NCH149 were 8.1, 15.1 and 8.87 μM, respectively (see Table 3 below). These values are slightly lower as compared to those found for Compound 1 as shown in Table 2 above, i.e. $IC_{50}$ of 11.4 and 17.3 μM for NCH82 and NCH89, respectively.

Thus, modifying the phosphaphenalene core by replacing the thiophene moiety with a pyrrole ring leads to an improved anti-proliferative activity in vitro. In line with the observations discussed above, replacing the chloride atom at the gold moiety by a sugar derivative remarkably increases the bio-activity of the drug (Table 2 and 3).

Compound 6 showed mean IC50 values one order of magnitude lower than Compound 5, reaching sub micromolar concentrations; i.e. 0.73, 4.00 and 0.87 μM for cell lines NCH82, NCH89 and NCH149, respectively (Table 3). Again, these values are notably lower than those of the analogue Compound 4 (Table 3), which contains a phosphaphenalene fused to a thiophene ring instead of a pyrrole heterocycle.

In turn, introducing a phenylsulfonyl fragment at the nitrogen of the phosphaphenalene core (Compound 8) leads to higher bio-activity compared to Compound 5. However, values are slightly lower than those of the N-methyl derivative Compound 6.

TABLE 3

Antiproliferative effects of Compounds 1, 4 to 6 and 8 upon treatment of cell lines from five different types of cancer (expressed as mean $IC_{50}$ values (μM) of three biological replicates ± standard deviation).

| Type of cancer cells | | Compound 1 | Compound 4 | Compound 5 | Compound 6 | Compound 8 |
|---|---|---|---|---|---|---|
| Glioblastomas | NCH82 | 11.4 ± 0.11 | 1.44 ± 0.16 | 8.1 ± 0.62 | 0.73 ± 0.12 | 1.37 ± 0.06 |
| | NCH89 | 17.3 ± 1.02 | 2.9 ± 0.41 | 15.1 ± 0.66 | 4.00 ± 0.26 | 4.49 ± 0.12 |
| | NCH149 | n.d. | 3.01 ± 0 | 8.87 ± 0.45 | 0.87 ± 0.12 | 2.85 ± 0.17 |
| Brain metastases | NCH517 | n.d. | n.d. | n.d. | 1.60 ± 0.30 | n.d. |
| | NCH604a | n.d. | n.d. | n.d. | 1.86 ± 0.14 | n.d. |
| | NCH466 | n.d. | n.d. | n.d. | 1.01 ± 0.02 | n.d. |
| Meningiomas | NCH93 | n.d. | n.d. | n.d. | 1.35 ± 0.09 | n.d. |
| | BenMen-1 | n.d. | n.d. | n.d. | 1.32 ± 0.12 | n.d. |
| IDH-mut. gliomas | NCH551b | n.d. | n.d. | n.d. | 1.23 ± 0.25 | n.d. |
| | NCH1618 | n.d. | n.d. | n.d. | 0.88 ± 0.29 | n.d. |
| | NCH3763 | n.d. | n.d. | n.d. | 5.21 ± 0.31 | n.d. |
| Head and neck cancers | HNO210 | n.d. | n.d. | n.d. | 1.10 ± 0.08 | n.d. |
| | HNO199 | n.d. | n.d. | n.d. | 2.65 ± 0.25 | n.d. |
| | HNO97 | n.d. | n.d. | n.d. | 5.51 ± 1.04 | n.d. |

n.d. = not determined

The mean $IC_{50}$ values for Compound 8 were 1.37, 4.49 and 2.85 μM for glioblastoma cell lines NCH82, NCH89 and NCH149, respectively (Table 3). Altogether, while there appears to be flexibility regarding the fused heterocycle at the phosphaphenalene core in order to maintain bioactivity, the specific type of the fused heterocycle at the phosphaphenalene core appears to influence the bio-activity of the drug. Specifically, pyrrole appears to lead to further improved cytotoxic activity.

In contrast, further increasing the bulkiness of the phosphaphenalene with an electron-accepting phenylsulfonyl group also largely maintains the agent's bioactivity but does not further enhance it.

Based on the remarkable results obtained with Compound 6, its anti-proliferative effects on a series of different cancer cell lines was investigated. To that end, in addition to the three glioblastoma cell lines described above, Compound 6 was employed on eleven other cancer cell lines including brain metastasis (NCH517, NCH604a and NCH466), meningioma (NCH93 and BenMen-1), IDH-mutant glioma (NCH511b, NCH1618 and NCH3763), and head and neck cancer cell lines (HNO210, HNO199 and HNO97) (Table 3).

Overall, Compound 6 showed excellent anti-proliferative effects on all cell lines, with mean $IC_{50}$ values in some cell lines around 1.5 μM, even including highly invasive brain metastatic cancer cells. Impressive results were obtained for IDH-mutant glioma cell line NCH1681 with $IC_{50}$ values of only 0.88 μM.

Motivated by these results, the capacity of Compound 6 to induce apoptosis in cancer cell lines derived from brain metastases, meningiomas, IDH-mutant gliomas and head and neck cancers was analyzed. For this purpose, cells were incubated with different concentrations of Compound 6 for 48 hours and subsequently analyzed by flow cytometry (see representative example in FIG. 4A). Annexin V and propidium iodide (PI) were used as indicators for apoptosis/necrosis.

Figure 4:
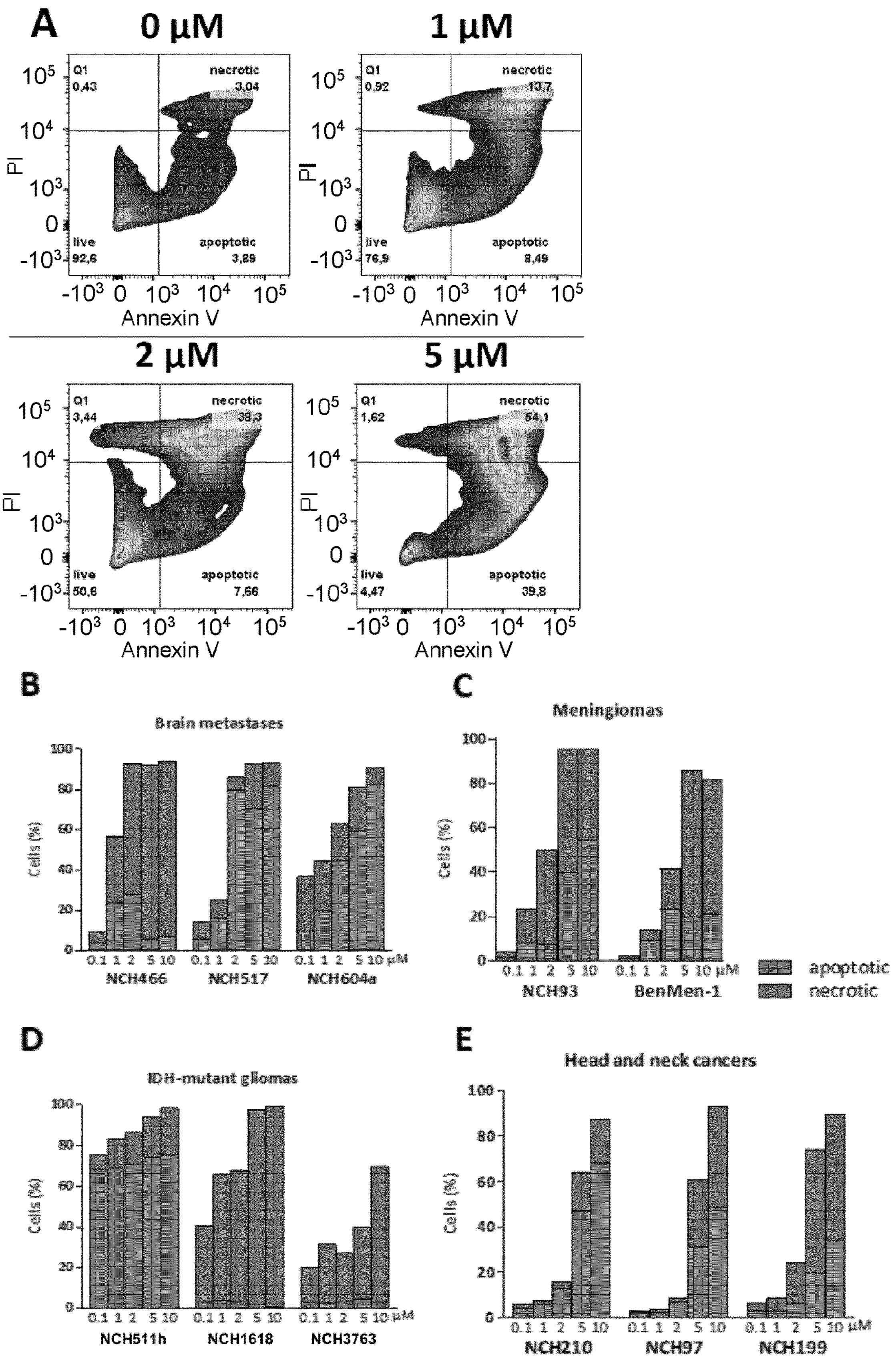
FIG. 4 shows (A) Flow cytometry analysis of NCH93 untreated cells and upon exposure to 1 μM, 2 μM, and 5 μM of Compound 6 for 48 hours, and stack charts summarizing the percentage of apoptotic and necrotic cells of (B) brain metastasis cell lines, (C) meningioma cell lines, (D) IDH-mutant glioma cell lines and (E) head and neck cancer cell lines.

As expected, Compound 6 was able to induce apoptosis/necrosis in all analyzed cell lines (FIG. 4). In line with the obtained $IC_{50}$ values (see Table 3 above), brain metastasis and meningioma cell lines appeared to be more sensitive than head and neck cancer cell lines. A drug concentration of 2 μM induced apoptosis/necrosis in more than 50% of cells among NCH466, NCH517, NCH604a and NCH93 (FIGS. 4B and 4C). On the other hand, a drug concentration of 5 μM was required to cause apoptosis/necrosis in more than 50% of cells in head and neck cancer cell lines (FIG. 4E).

In addition to these surprising and excellent results, the inventive compounds demonstrated very high stability as shown by experimental tests with Compounds 6 and 8 under controlled thermodynamic conditions upon repetitive cycles of illumination (data not shown).

Based on the observed high bio-activity and the spectroscopic properties of Compound 6 as an example of the present invention, the drug uptake kinetics was investigated in NCH82 cell line. To this end, cells were treated with increasing concentrations of Compound 6 and its drug uptake was monitored with a fluorescence microscope (excitation/emission 350/455 nm; data not shown).

Surprisingly, after only 1 hour of treatment with 10 μM of Compound 6; i.e. a concentration above the $IC_{50}$ value, cells were able to internalize the compound and start shrinking and detaching. Cells treated with 1 μM of Compound 6 started to absorb the compound after 1 hour but their death could be observed only after 24 hours. When used at a concentration of 0.1 μM, Compound 6 started to be internalized after 24 hours but dead cells were first observed 48 hours after treatment initiation.

In summary, the results presented herein demonstrate that the bio-activity of the inventive phosphaphenalene gold complexes may be influenced and improved by subtle chemical modification of their structural features. Their unique properties allow for adjusting the electronic distribution over the 7-extended core, the bulkiness of the molecules and their photophysical properties.

In particular, pyrrole-fused phosphaphenalene derivatives appear to lead to further improved performance than thiophene-based analogs; it is worth noting that all these compounds are stable for weeks. Also, sugar derivatives attached to the gold atom provide further increased bio-activity in comparison to chloride atoms. Overall, phosphophenalene gold complexes as described and claimed herein possess a remarkable, unprecedented and surprising anti-proliferative capacity.

They inhibit the proliferation of 14 different tumor cell lines derived from glioblastomas, brain metastases, meningiomas, IDH-mutant gliomas and head and neck cancers. In addition, said compounds appear to sensitize cancer cell lines to apoptosis and demonstrate efficient uptake into cells.

Taken together, the broad applicability and high bioactivity of the phosphaphenalene gold complexes of the present invention in combination with their notable spectroscopic properties make it plausible that these compounds can suitably be used to provide promising therapeutics for improved treatments of lethal disease.

The structural modifications comprised by the scope of the present invention have substantially the same solvation shell radius of the claimed compounds which have been tested experimentally. These modifications merely slightly modify lipophilicity of the complexes. However, due to the relative small size of all complexes according to the present invention, the changes of lipophilicity are not expected to lead to substantial differences regarding the cytotoxic effects.

All compounds comprised by the scope of the present invention display comparable electronic density at the phosphorous center to hold/coordinate the active gold atom which is responsible for the anticancer effects. Therefore, it is deemed reasonable and plausible that all compounds currently claimed exhibit similar technical effects based on similar structural characteristics.

Examples

In the following, experimental details regarding the synthesis and characterization of the aforementioned compounds are provided.

General Information

All reactions were carried out in dry glassware and under inert atmosphere of purified argon or nitrogen using Schlenk techniques. Solvents such as $CH_2Cl_2$ and THF were used directly from a solvent purification system MB SPS-800. AcOEt, ethanol acetone were purchased from commercial suppliers and used as received. Potassium ethyl xanthogenate, $AgNO_3$, KSCN, 1-thio-β-D-glucose tetraacetate, magnesium sulfate, were purchased from commercial suppliers and used as received.

NMR Measurements:

$^{1}H$, $^{13}C$, $^{1}$ and $^{31}P$ NMR spectra were recorded on a Bruker Avance DRX-300, Bruker Avance 500 or Bruker Avance 600. Chemical shifts are expressed as parts per million (ppm, δ) and referenced to external 85% $H_3PO_4$ ($^{31}P$), or solvent signals ($^{1}H/^{13}C$): $CD_2Cl_2$ (5.33/53.80 ppm) as internal standards. Signal descriptions include: s=singlet, d=doublet, t=triplet, m=multiplet and br=broad. All coupling constants are absolute values and J values are expressed in Hertz (Hz).

Mass Spectrometry:

MS and HRMS were measured at the Organisch-Chemisches Institut of the Heidelberg University. A Bruker ApexQe hybrid 9.4 T FT-ICR was used for DART spectra and a JEOL AccuTOFGCx time-of-flight for EI spectra.

Steric Hindrance of Phosphorus Ligands:

Calculations of the buried volume % V were carried out by using a free web application software (http://www.molnac.unisa.it/OMtools/sambvca.php) and considering 3.50 Å as sphere radius. Hydrogen atoms were omitted and scaled Bondi radii were 1.7. The software is presented by Poater, B. et al., "*SambVca: A Web Application for the Calculation of the Buried Volume of N-Heterocyclic Carbene Ligands*", Eur. J. Inorg. Chem., 2009, pages 1759-1766.

X-Ray Crystallography:

X-ray crystal structure analyses were measured on Bruker Smart CCD or Bruker Smart APEX instrument using Mo-Kα radiation. Diffraction intensities were corrected for Lorentz and polarization effects. An empirical absorption correction was applied using SADABS (Program SADABS 2008/1 for absorption correction; G. M. Sheldrick, Bruker Analytical X-ray-Division, Madison, Wisconsin 2012) based on the Laue symmetry of reciprocal space.

Heavy atom diffractions were solved by direct methods and refined against F2 with the full matrix least square algorithm. Hydrogen atoms were either isotropically refined or calculated. The structures were solved and refined using the SHELXTL[S 2] software package. Crystal structure of Compound 2 was obtained from DCM/pentane at room temperature and crystal structure of Compound 3 from DCM solutions by slow evaporation at room temperature. Supplementary crystallographic data for these compounds can be obtained free of charge from The Cambridge Crystallographic Data Centre via www.ccdc.cam.ac.uk/data_request/cif—CCDC 1832813 (Compound 2) and 1832814 (Compound 3).

Cell Culture Conditions:

Adherently growing cell lines derived of glioblastomas (NCH82, NCH89 and NCH149), brain metastases (NCH466, NCH517 and NCH604a), meningiomas (NCH93 and Ben-Men-1 (DSMZ, Braunschweig, Germany)) and head and neck cancers (HNO97, HNO199 and HNO210) as well as stem-like cell lines derived of IDH-mutant gliomas (NCH551b, NCH1618 and NCH3763) were characterized and cultured as already described (B. Campos et al., *Clin. Cancer Res.* 2010, 16 (10), 2715-2728. https://doi.org/10.1158/1078-0432.CCR-09-1800; P. Dao Trong et al., *IJMS* 2018, 19 (10), 2903. https://doi.org/10.3390/ijms19102903; Y. Jungwirth et al., *Cancers* 2019, 11 (4), 545. https://doi.org/10.3390/cancers11040545; S. Karcher et al., *Int. J. Cancer* 2006, 118 (9), 2182-2189. https://doi.org/10.1002/ijc.21648; and C. Rapp et al., *Acta Neuropathol.* 2017, 134 (2), 297-316. https://doi.org/10.1007/s00401-017-1702-1).

Adherent growing cell lines (NCH82, NCH89, NCH210, and NCH125) as well as glioma stem-like cell lines (NCH421k, NCH644, NCH660h) were established from intraoperatively obtained glioblastoma samples characterized and cultured as already described (S. Karcher et al., Int. J. Cancer. 2006, 118, 2182-2189; C. Rapp et al., Acta Neuropathol. 2017, 134, 297-316; and B. Campos et al., Clin. Cancer Res. 2010, 16, 2715-2728). Cell lines were authenticated and written informed consent was obtained from patients according to the research proposals approved by the Institutional Review Board at the Medical Faculty of the University of Heidelberg.

Proliferation Assay—Adherent Cell Lines:

The effect of different compounds on cell growth was evaluated by the crystal violet method as described earlier (J. P. Rigalli et al., Cancer Lett. 2016, 376, 165-172). Briefly, cells were seeded in 96-well plates (10,000 cells/well). After 24 h cell culture medium was replaced by fresh compound-containing medium (ten different concentrations (0.01 to 200 μM μM)). After 48 h of exposure extent of cell proliferation inhibition was determined by crystal violet staining of surviving cells. Therefore, cells were washed and stained with 0.5% crystal violet solution (2.5 g in 100 ml methanol, diluted with 400 ml aqua bidest) for 15 min, rinsed and dried overnight.

Next, crystal violet was solubilized in methanol and absorbance was measured at 555 nm. The proliferative index was calculated as crystal violet absorption intensity as percentage relative to baseline (no cells) as described before (T. Peters et al., Naunyn Schmiedebergs Arch Pharmacol. 2006, 372, 291-299.) Cell survival plotted against the decimal logarithm of drug concentration in μM (c (of compound x) in μM) and fitted to a sigmoidal dose-response curve using Graph Pad Prism 7.02 (GraphPad Software, San Diego, USA).

Proliferation Assay—Glioma Stem-Like Cell (GSC) Lines:

To assess the effect of Compound 4 and Compound 6 on cell growth of glioma stem-like cells (GSC) and GSC lines derived from IDH-mutant gliomas, cellular ATP levels were measured using the luminescent CellTiter-Glo Assay (Promega Corp, Madison, WI). GCS spheroid cultures were gently dissociated and cell suspensions were seeded in 96-well tissue culture plates (8,000 cells/well, 100 μl/well). After a 24-hour incubation period without any compound freshly reconstituted compound in ten final concentrations ranging from 0.01 μM to 200 μM were added and cells were incubated for 48 hours.

Before measurement, the plate was equilibrated at room temperature for 30 minutes. Then, 100 μl of CellTiter-Glo Reagent were added to each well and the plate was placed on an orbital shaker for 2 minutes to mix the content. Next, the plate was incubated for 10 minutes at room temperature and finally, the luminescence was measured. Cell viability was plotted against the decimal logarithm of drug concentration in μM (c (of Compound 4/Compound 6) μM) and fitted to a sigmoidal dose-response curve using Graph Pad Prism 7.02 (GraphPad Software, San Diego, USA).

Effect of Drugs on Apoptosis (Annexin V Apoptosis Assay):

To quantitate the extent of apoptosis and necrosis, either annexin V staining combined with DAPI or double labeling of cells with annexin V and propidium iodide (PI) was used. The double labeling allows the distinction between apoptotic (annexin $V^{pos}/DAPI^{neg}$ or annexin $V^{pos}/PI^{neg}$) and necrotic (annexin $V^{pos}/DAPI^{pos}$ or annexin $V^{pos}/PI^{pos}$) cells. Cells were seeded in a 6-well plate ($2.5\times10^5$/well) and left to attach overnight. Medium was replaced by fresh medium containing defined drug concentrations or compound solvent DMSO (untreated control) and incubated for 24 h. As positive control cells were treated with 1 μM of the apoptosis-inducing reagent staurosporin (#9953, Cell Signaling Technology, Danvas, USA).

After treatment supernatant containing apoptotic and necrotic cells was collected, cells were harvested, washed, and up to $1\times10^6$ cells were incubated with FITC-conjugated annexin V antibody diluted in 1:1000 DAPI solution following manufactures instructions (#51-65874X, BD Biosciences, Franklin Lakes, USA) or incubated with FITC-conjugated annexin V antibody and PI for 15 min following manufacturer instructions (#51-65974X, BD Biosciences, Franklin Lakes, USA). Cells were acquired by flow cytometry using a BD LSRII flow cytometer (BD Bioscienes, Franklin Lakes, USA) and analyzed by FlowJo Software v7.6.5 (TreeStar, Ahland, USA).

Effect of Drugs on Glioma Cell Migration (Scratch Assay):

To assess the effect of the drugs on cell migration in vitro cells were seeded in 6-well plates ($5\times10^5$/Well) and left to attach. On the next day the cell monolayer was scraped in a straight line to create a "scratch" with a p200 pipet tip. Debris was removed by washing the cells and medium was replaced with 5 ml compound-containing medium in three different cell line specific concentrations ($IC_{50}$, $IC_{50}/2$, $IC_{50}/10$) for 24 h. Phase contrast images were acquired at 0 h and after 12 h of exposure to the respective drug concentration using a BX50 microscope with a SC30 camera (both Olympus, Tokyo, Japan). The cell-free areas at both time points were quantified and compared using the imaging software cellSens (Olympus, Tokyo, Japan).

Drug Uptake Kinetics:

To measure the uptake kinetics of compound 6 by NCH82 cells, they were seeded in a 96-well plate (5,000 cells/well) and after 24 h, cell culture medium was replaced with compound 6 or DMSO-containing medium (0.1, 1 and 10 μM). Images were taken with a fluorescence microscope (Olympus, Shinjuku, Japan) at 1 h, 24 h and 48 h after treatment initiation. A laser with an excitation/emission spectrum of 350/455 nm was used and images were taken with a 10× objective.

Synthetic Procedures

Compound 1 was prepared as previously reported by Romero-Nieto C. et al., Angew. Chem. Int. Ed. 2015, cited above—designated as gold complex 16.

Compound 2

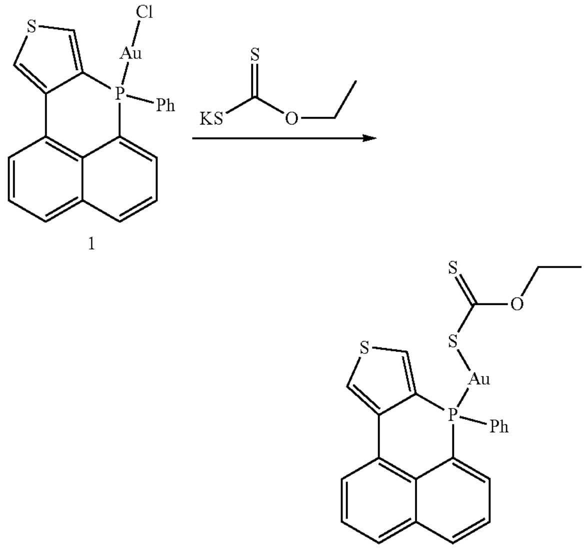

1

2

Compound 1 (1 eq, 0.076 mmol, 42 mg) was dissolved in 4 mL of DCM and potassium ethyl xanthogenate (1 eq, 0.076 mmol, 12 mg) was added at room temperature. The crude was stirred 1.5 hours. Then, the mixture was washed with water, dried over $MgSO_4$ and the volatiles were removed under reduced pressure. The crude was washed with AcOEt×3 and crystalized by slow evaporation from DCM solutions. Yield: 88% (42 mg, 0.066 mmol).

$^1$H-NMR (600 MHz, $CD_2Cl_2$): δ 8.26 (ddd, J=18.8, 7.0, 1.2 Hz, 1H), 8.21 (dd, J=7.4, Hz, 1H), 8.17 (dd, J=8.8, 2.9 Hz, 1H), 8.07 (dd, J=2.9, 1.1 Hz, 1H), 8.04 (d, J=8.2 Hz, 1H), 7.93 (d, J=8.2 Hz, 1H), 7.66 (t, J=7.8 Hz, 1H), 7.63-7.61 (m, 1H), 7.42 (ddd, J=13.7, 8.3, 1.1 Hz, 2H), 7.33 (td, J=7.4, 2.0 Hz, 1H), 7.26 (td, J=7.5, 2.5 Hz, 2H), 4.55-4.50 (m, 2H), 1.40 (d, J=14.2 Hz, 3H).

$^{13}C\{^1H\}\{^{31}P\}$ NMR (151 MHz, $CD_2Cl_2$): δ 138.3 (s, 1C), 136.8 (s, 1C), 136.1 (s, 1C), 135.2 (s, 1C), 134.5 (s, 1C), 133.6 (s, 1C), 132.4 (s, 1C), 131.6 (s, 1C), 129.9 (s, 1C), 129.4 (s, 1C), 128.4 (s, 1C), 127.6 (s, 1C), 127.2 (s, 1C), 126.2 (s, 1C), 124.8 (s, 1C), 124.6 (s, 1C), 123.0 (s, 1C), 123.0 (s, 1C), 70.6 (s, 1C), 14.3 (s, 1C).

$^{31}$P-NMR (243 MHz, $CD_2Cl_2$): δ 6.55.

HRMS (EI+) calculated for $C_{10}H_4Br_4O_2^+$ 471.6939, found 471.6940.

Compound 3

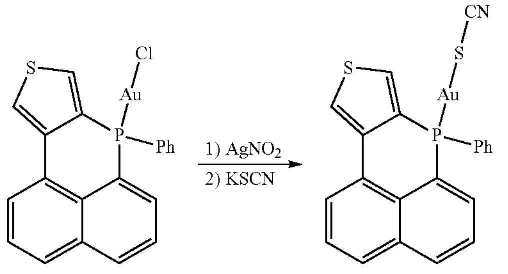

1

3

Compound 1 (1 eq, 0.273 mmol, 150 mg) was suspended in 4 mL of ethanol and mixed with $AgNO_3$ (1 eq, 0.273 mmol, 46 mg) dissolved in 4 ml of water. The mixture was stirred one hour and 5 mL of DCM were added. After stirring for 30 min, 804 of KSCN 8M in water. The mixture was stirred during one hour, the DCM phase was separated and the aqueous phase was extracted three times with DCM. After drying over $MgSO_4$, the crude was concentrated under reduced pressure and filtered through Celite. The product was purified by column chromatography using silica and eluent mixtures from DCM/pentane 6:4 to pure DCM and crystallized from a DCM/pentane mixture. Yield: 65% (102 mg, 0.179 mmol).

$^1$H-NMR (600 MHz, $CD_2Cl_2$): δ 8.26 (d, J=7.4 Hz, 1H), 8.18 (dd, J=19.1, 7.0 Hz, 1H), 8.13 (dd, J=6.6, 3.3 Hz, 2H), 8.09 (d, J=8.2 Hz, 1H), 7.97 (d, J=8.1 Hz, 1H), 7.71-7.65 (m, 2H), 7.42-7.37 (m, 3H), 7.31 (td, J=7.8, 2.2 Hz, 2H).

$^{13}C\{^1H\}\{^{31}P\}$ NMR (151 MHz, $CD_2Cl_2$): δ 138.2 (s, 1C), 136.9 (s, 1C), 136.3 (s, 1C), 134.6 (s, 1C), 134.1 (s, 1C), 134.0 (s, 1C), 132.6 (s, 1C), 132.1 (s, 1C), 130.1 (s, 1C), 129.6 (s, 1C), 128.3 (s, 1C), 127.4 (s, 1C), 126.2 (s, 1C), 125.0 (s, 1C), 123.3 (s, 1C), 123.3 (s, 1C), 121.9 (s, 1C).

$^{31}$P-NMR (243 MHz, $CD_2Cl_2$): δ 7.10.

HRMS (EI+) calculated for $C_{10}H_6Br_2O_2^+$ 315.87291, found 315.8737.

Compound 4

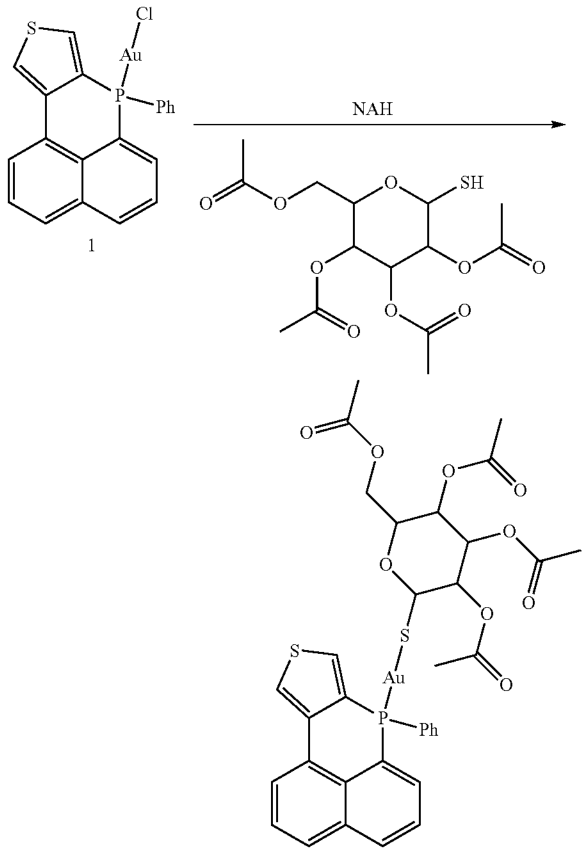

NaH was added to 1-thio-β-D-glucose tetraacetate (1 eq, 0.182 mmol, 66 mg) in 5 mL of THF at room temperature. The mixture was stirred one hour, filtered through Celite via cannula and added to compound 1 (0.9 eq, 0.164 mmol, 90 mg) dissolved in 5 mL of THF at room temperature. The solution was stirred 1.5 hours and the solvent removed under vacuum. The crude was dissolved in DCM, filtered through Celite and subjected to column chromatography using silica and AcOEt/acetone 8:2 as eluent. Yield: 72% (104 mg, 0.118 mmol).

$^1$H-NMR (600 MHz, $CD_2Cl_2$): δ 8.31-8.24 (m, 3H), 8.12 (ddd, J=6.2, 2.9, 1.1 Hz, 1H), 8.06 (dd, J=8.2, 1.2 Hz, 1H), 7.94 (s, 1H), 7.69-7.64 (m, 2H), 7.45-7.39 (m, 2H), 7.35-7.32 (m, 1H), 7.30-7.26 (m, 2H), 5.20-5.14 (m, 2H), 5.08 (dt, J=13.1, 9.5 Hz, 2H), 4.14 (qd, J=12.0, 3.7 Hz, 2H), 3.77 (ddd, J=10.0, 5.0, 2.5 Hz, 1H), 2.07 (s, 3H), 2.00 (s, 3H), 1.98 (s, 3H), 1.91 (s, 3H).

$^{13}C\{^1H\}\{^{31}P\}$ NMR (151 MHz, $CD_2Cl_2$): δ 170.3 (s, 1C), 169.9 (s, 1C), 169.5 (s, 1C), 169.4 (s, 1C), 137.9 (s, 1C), 137.9 (s, 1C), 136.4 (s, 1C), 136.32 (s, 1C), 135.6 (s, 1C), 135.5 (s, 1C), 135.1 (s, 1C), 135.1 (s, 1C), 134.2 (s, 1C), 134.1 (s, 1C), 133.0 (s, 1C), 132.0 (s, 1C), 132.0 (s, 1C), 131.1 (s, 1C), 131.1 (s, 1C), 129.5 (s, 1C), 129.0 (s, 1C), 128.9 (s, 1C), 128.1 (s, 1C), 127.2 (s, 1C), 126.7 (s, 1C), 124.3 (s, 1C), 122.8 (s, 1C), 122.8 (s, 1C), 122.5 (s, 1C), 122.4 (s, 1C), 83.0 (s, 1C), 77.6 (s, 1C), 75.7 (s, 1C), 73.9 (s, 1C), 68.7 (s, 1C), 62.6 (s, 1C), 20.9 (s, 1C), 20.4 (s, 1C), 20.4 (s, 1C), 20.4 (s, 1C).

$^{31}$P-NMR (122 MHz, $CDCl_3$)

HRMS (EI+) calculated for $C_{10}H_6Br_2O_2^+$ 315.8729, found 315.8728.

Synthesis of Compound 5

In a baked-out 10 mL one neck round-bottom flask connected to the schlenk adapter, 2-(8-bromonaphthalen-1-yl)-1-methyl-1H-pyrrole (1.0 eq, 0.18 mmol, 52 mg) was dissolved in 3.6 mL of dry $Et_2O$ and cooled to −80° C. Then, $^t$BuLi (1.0 eq, 0.18 mmol, mL, 1.7 M in pentane) was added dropwise.

Immediately afterwards, the lithiated 2-(8-bromonaphthalen-1-yl)-1-methyl-1H-pyrrole was reacted with $PhPCl_2$ (1.05 eq, 0.19 μmol, 26 μL, 97%) and the reaction mixture was stirred for 1 hour at room temperature. The solvent was removed under vacuum, 4.5 mL of DCM and chloro(dimethylsulfide)gold(I) (DMS-AuCl) (1.0 eq., 0.18 mmol, 53 mg) were subsequently added, and the reaction mixture was stirred for additional 1.5 hours.

The solvent was removed under vacuum again to give pale brown solid. After purification by column chromatography using alumina and DCM:pentane (7:3) mixture as eluent 76 mg (0.14 mmol) of a yellow solid were isolated (Yield: 78%).

$^1$H NMR (400 MHz, $CDCl_3$): δ 8.17 (dd, J=18.4, 6.7 Hz, 2H), 8.02 (d, J=7.3 Hz, 1H), 7.96 (d, J=8.1, 1H), 7.80 (d, J=8.51 Hz, 1H), 7.61-7.58 (m, 2H), 7.49 (dd, J=14.0, 7.0 Hz, 2H), 7.33-7.30 (m, 1H), 7.26-7.24 (m, 2H), 6.92 (t, J=7.3 Hz, 1H), 6.53 (dd, J=5.5, 2.8 Hz, 1H), 4.12 (s, 3H).

$^{13}C\{^1H\}$ and DEPT 135 NMR (101 MHz, $CDCl_3$): δ 136.9 (d, CH), 135.3 (s, C), 134.7 (s, C), 134.3 (d, C), 133.2 (d, CH), 133.0 (d, CH), 132.3 (d, CH), 131.2 (d, CH), 129.8 (d, CH), 129.0 (d, CH), 128.9 (s, CH), 128.7 (d, CH), 126.1 (s, C), 126.0 (d, CH), 125.0 (d, C), 124.2 (s, C), 123.6 (s, C), 127.7 (d, CH), 112.4 (d, CH), 106.0 (d, C), 39.4 (s, $CH_3$).

$^{31}P\{^1H\}$ NMR (162 MHz, in $CDCl_3$): δ 2.64. HRMS (FAB) m/z: $[M^{\bullet+}]$ calcd for $[C_{21}H_{16}AuClNP]^{\bullet+}$ 545.0374, found 545.0404.

Synthesis of Compound 6

In a baked-out schlenk tube, 1-thio-β-D-glucose tetraacetate (1.0 eq, 0.061 mmol, 22 mg) was dissolved in 2 mL of dry THF. Then, NaH (2.0 eq, 0.122 mmol, 3 mg) was added and reaction mixture was stirred for 1 hour. The resulting suspension was filtered through Celite under inert atmosphere to a baked-out schlenk tube containing Compound 5 (0.9 eq, 0.055 mmol, 30 mg) dissolved in 1.6 mL of dry THF.

After stirring during 1.5 hours, the solvent was removed under vacuum. Purification by column chromatography using alumina and EtOAc:DCM (2:8) mixture as eluent afforded 35 mg (0.04 mmol) of a yellow solid (Yield: 73%).

$^1$H NMR (600 MHz, $CDCl_3$): δ 8.28 (dd, J=18.2, 7.0 Hz, 1H), 8.02 (d, J=7.5 Hz, 1H), 7.95 (d, J=8.1 Hz, 1H), 7.79 (d, J=8.2 Hz, 1H), 7.65-7.57 (m, 2H), 7.56-7.50 (m, 2H), 7.35-7.28 (m, 3H), 6.94 (dt, J=4.1, 2.7 Hz, 1H), 6.65 (ddd, J=8.0, 5.4, 2.8 Hz, 1H), 5.23-5.10 (m, 4H), 4.22 (dd, J=12.2, 4.7 Hz, 1H), 4.14 (d, J=2.1 Hz, 1H), 4.12 (d, J=1.4 Hz, 3H), 3.77 (ddd, J=9.2, 4.5, 2.2 Hz, 1H), 2.09 (s, 3H), 2.01 (d, J=10.7 Hz, 6H), 1.88 (s, 3H).

$^{13}C\{^1H\}$ and DEPT 135 NMR (101 MHz, $CDCl_3$): δ 171.2 (s, C), 170.7 (s, C), 170.0 (d, C), 137.0 (dd, CH), 134.6 dd, C), 133.6 (d, C), 133.3 (0, CH), 132.6 (dd, CH), 131.2 (s, CH), 129.9 (dd, CH), 129.4 (s, C), 129.2 (d, CH), 129.0 (s, CH), 127.3 (d, CH), 126.4 (d, CH), 126.3 (s, CH), 125.6 (d, C), 122.7 (s, CH), 112.8 (dd, CH), 83.4 (s, CH), 77.9 (s, CH), 76.0 (s, CH), 74.6 (s, CH), 69.2 (s, CH), 63.1 (s, $CH_2$), 39.7 (s, $CH_3$), 21.5 (s, $CH_3$), 21.0 (d, $CH_3$).

$^{31}P\{^1H\}$ NMR (162 MHz, in $CDCl_3$): δ 9.11. HRMS (DART$^+$): [$M^{•+}$] calcd for $[C^{35}H^{35}AuNO^9PS]^{•+}$ 873.1436, found 874.1494.

Synthesis of Compound 7

In a baked-out schlenk tube 2-(8-bromonaphthalen-1-yl)-1-(phenylsulfonyl)-1H-pyrrole (1.0 eq, 102 μmol, 42 mg) was dissolved in 5 mL of dry $Et_2O$ and cooled to −90° C. Then, $^n$BuLi (1.0 eq, 102 μmol, 0.06 mL, 1.7 M in pentane) was added dropwise. Immediately afterwards, the lithiated intermediate was reacted with $PhPCl_2$ (1.0 eq, 102 μmol, 14 μL, 97%) and the reaction mixture was stirred for 1 hour at room temperature.

The solvent was removed under vacuum, 2 mL of DCM and chloro(dimethylsulfide) gold(I) (DMS-AuCl) (1.0 eq, 102 μmol, 30 mg) were added, and the reaction mixture was stirred for an additional hour. The solvent was removed under vacuum again to give brown solid. After purification by column chromatography using silica and DCM as eluent, 24 mg (36 μmol) of a yellow solid were isolated (Yield: 51%).

$^1H$ NMR (400 MHz, $CDCl_3$): δ 8.70 (d, J=7.4 Hz, 1H), 8.05 (dd, J=18.7, 7.1 Hz, 1H), 7.96 (d, J=8.2 Hz, 1H), 7.84 (d, J=8.3 Hz, 1H), 7.80 (t, J=3.6 Hz, 1H), 7.65-7.54 (m, 3H), 7.49 (dd, J=7.6, 3.8 Hz, 3H), 7.39-7.28 (m, 6H), 6.67 (dd, J=4.5, 3.6 Hz, 1H).

$^{13}C\{^1H\}$ and DEPT 135 NMR (101 MHz, $CDCl_3$): δ 137.7 (d, C), 137.0 (s, C), 136.5 (d, CH), 134.6 (s, CH), 133.6 (d, C), 133.3 (s, CH), 132.4 (s, CH), 132.3 (s, CH), 131.9 (s, CH), 130.8 (s, CH), 130.6 (s, CH), 129.2 (s, CH), 129.1 (s, CH), 128.6 (s, CH), 126.9 (s, CH), 126.1 (s, CH), 125.9 (s, CH), 122.2 (d, C), 115.6 (d, CH).

$^{31}P\{^1H\}$ NMR (162 MHz, in $CDCl_3$): δ 5.57. HRMS (ESI$^+$) m/z: [$M^{•+}$] calcd for $[C_{26}H_{18}AuClNO_2PS]^{•+}$ 671.0150, found 671.0205.

Synthesis of Compound 8

1-thio-ß-D-glucose tetraacetate (1.0 eq, 0.041 mmol, 15 mg) was dissolved in baked-out schlenk tube with 1.4 mL of dry THF. Then, NaH (2.0 eq, 0.082 mmol, 2 mg) was added and reaction mixture was stirred for 1 hour. The resulting suspension was filtered through Celite under inert atmosphere to a baked-out schlenk tube containing Compound 7 (0.9 eq, 0.037 mmol, 25 mg) dissolved in 1.1 mL of dry THF.

After stirring 1.5 hours, the solvent was removed under vacuum. Purification by column chromatography using alumina and EtOAc:pentane (6:4) mixture as eluent 20 mg (0.02 mmol) afforded a yellow solid (Yield: 54%).

$^1H$ NMR (600 MHz, $CDCl_3$): δ 8.70 (dd, J=7.4, 4.3 Hz, 1H), 8.16 (ddd, J=18.2, 6.3, 3.5 Hz, 1H), 7.94 (d, J=8.1 Hz, 1H), 7.82 (dt, J=7.2, 3.5 Hz, 2H), 7.61-7.55 (m, 2H), 7.53-7.48 (m, 2H), 7.47 (d, J=7.5 Hz, 1H), 7.42-7.28 (m, 6H), 6.82-6.77 (m, 1H), 5.21-5.09 (m, 4H), 4.23 (dd, J=12.2, 4.7 Hz, 1H), 4.13 (d, J=12.0 Hz, 1H), 3.78 (dd, J=7.2, 2.2 Hz, 1H), 2.09 (s, 3H), 2.02 (d, J=14.8 Hz, 7H), 1.88 (s, 3H).

$^{13}C\{^1H\}$ and DEPT 135 NMR (101 MHz, $CDCl_3$): δ 171.6 (d, C), 170.6 (s, C), 170.1 (s, C), 170.0 (s, C), 137.5 (d, C), 136.7 (t, CH), 134.8 (s, CH), 133.8 (t, C), 133.3 (s, CH), 132.7 (dd, CH), 131.9 (s, CH), 130.8 (dd, CH), 129.5 (dd, CH), 129.2 (s, CH), 128.5 (d, CH), 127.3 (d, CH), 126.4 (d, CH), 126.2 (s, CH), 122.6 (t, C), 116.0 (s, CH), 83.5 (s, CH), 76.1 (s, CH), 74.5 (s, CH), 69.2 (s, CH), 63.1 (s, $CH_2$), 21.5 (s, $CH_3$), 21.1 (d, $CH_3$).

$^{31}P\{^1H\}$ NMR (162 MHz, in $CDCl_3$): δ 9.45. HRMS (ESI$^+$) m/z: [$M^{•+}$] calcd for $[C_{40}H_{37}AuNO_{11}PS_2Na]^{•+}$ 1022.1109, found 1022.1122.

The invention claimed is:

1. A method of treating brain cancer, or head and neck cancer in a subject in need thereof, comprising administering to the subject a therapeutically effective amount of a compound of Formula (A), (A)

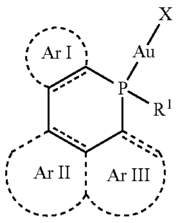

wherein

Ar I represents a monocyclic aromatic moiety selected from the group consisting of phenyl, pyridine, pyrrole, N-substituted pyrrole, wherein the substituent on the nitrogen atom is methyl or phenylsulfonyl, furan and thiophene, or represents a bicyclic aromatic moiety selected from the group consisting of naphthalene, indole and benzothiophene, wherein Ar I may be substituted by one or more substituents selected from the group consisting of a halogen atom, a five- or six-membered aromatic heterocycle containing N, S or O, a $C_{1-6}$ aliphatic group and a $C_{3-6}$ cycloaliphatic group, wherein the $C_{1-6}$ aliphatic group and/or the $C_{3-6}$ cycloaliphatic group may additionally contain one or more heteroatoms selected from N, S and O, Ar II and Ar III each independently represent a benzene group, a pyridine group, a pyrrole group, a N-substituted pyrrole group wherein the substituent on the nitrogen atom is methyl or phenylsulfonyl or a thiophene group;

$R^1$ represents an aromatic group, a hydroxy group, a $C_1$-$C_6$ alkyl group or a $C_1$-$C_6$ alkoxy group; and X is selected from the group consisting of sugars, albumins, halogen atoms, $CH_3$, $NO_3$, CN, and $SR^3$, wherein $R^3$ is selected from the group consisting of 2,3,4,6-tetra-O-acetyl-β-D-glucopyranosyl, β-D-glucopyranosyl, 2,3,4,6-tetramesyl-β-D-gluco-pyranosyl, 2,3,4,6-tetra-O-acetyl-α-D-glucopyranosyl, 2,3,4,6-tetra-O-acetyl-β-D-galacto-pyranosyl, hepto-O-acetyl-β-maltosyl, 1,2-O-isopropylidene-5-α-D-xylo-furanosyl, C1-C8 alkyl, CH(CO2H)CH2CO2H, 2-morpholinoethyl, 2'-ethyl-1-β-D-glucopyranosyl, 2'-ethyl-1-thio-β-D-glucopyranosyl, glutathionyl hydrochloride, CN, C(NH2)2·HCl, C(NH2)NHNH2, phenyl, 1-aminophenyl, 2-pyridyl, 6-methyl-2-pyridyl, 4-pyridyl, thiazoline-2-yl, 4,5-dihydrothiazol-2-yl, 1H-benzimidazol-2-yl, benzoxazol-2-yl, benzothiazol-2-yl, (CH2CH2OH)2NO$_3$, pyrimidin-2-yl, 4-methylpyrimidin-2-yl, 4,6-dimehylpyrimidin-2-yl, 1,2-dihydropyridin-2-yl, 1,2-dihydropyrimidin-2-yl, 9H-purin-6-yl, 2-amino-9H-purin-6-yl, and $(NH_2)_2C$=.

2. The method according to claim 1, wherein Ar II and Ar III together represent a naphthalene group, an indole group, a N-substituted indole group, a quinoline group, or a benzothiophene group.

3. The method according to claim 1, wherein Ar II and Ar III together represent a naphthalene group.

4. The method according to claim 1, wherein Ar I is a benzene group, a naphthalene group, a thiophene group, a furan group, a pyrrole group, a benzothiophene group, or a pyridine group, and wherein Ar I may be substituted by one or more substituents selected from the group consisting of a halogen atom, a five- or six-membered aromatic heterocycle containing N, S or O, a $C_{1-6}$ aliphatic group and a $C_{3-6}$ cycloaliphatic group, wherein the $C_{1-6}$ aliphatic group and/or the $C_{3-6}$ cycloaliphatic group may additionally contain one or more heteroatoms selected from N, S and O.

5. The method according to claim 1, wherein Ar I is a thiophene group.

6. The method according to claim 1, wherein Ar I is a pyrrole group.

7. The method according to claim 1, wherein X is selected from the group consisting of Cl, xanthate, thiocyanide, and 3,4,5-triacetyloxy-6-(acetyloxymethyl) oxane-2-thiolate.

8. The method according to claim 1, wherein X is xanthate or 3,4,5-triacetyloxy-6-(acetyloxymethyl) oxane-2-thiolate.

9. The method according to claim 3, wherein Ar I is an N-substituted pyrrole group with a methyl group as substituent on the N atom, wherein $R^1$ is a phenyl group, and wherein X is 3,4,5-triacetyloxy-6-(acetyloxymethyl) oxane-2-thiolate.

10. The method according to claim 1, wherein the protecting groups of Ar I, Ar II and Ar III are selected from $Si(CH_3)_3$, $SO_2Ph$ and sugars.

11. A compound of Formula (B), (B)

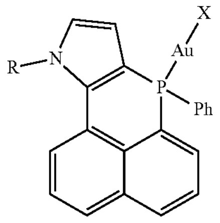

wherein R is methyl or $SO_2Ph$, and wherein X is chloride or 3,4,5-triacetyloxy-6-(acetyloxymethyl) oxane-2-thiolate.

12. The compound according to claim 11, wherein R is methyl and wherein X is 3,4,5-triacetyloxy-6-(acetyloxymethyl) oxane-2-thiolate.

13. A method of treating brain cancer, or head and neck cancer in a subject in need thereof, comprising administering to the subject a therapeutically effective amount of a compound according to claim 11.

14. The method according to claim 1, wherein the brain cancer is selected from glioblastoma, brain metastasis, meningioma, or IDH-mutant glioma.

15. A pharmaceutical composition comprising a compound of Formula (A), (A)

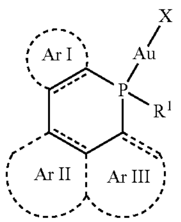

wherein

Ar I represents a monocyclic aromatic moiety selected from the group consisting of phenyl, pyridine, pyrrole, N-substituted pyrrole, wherein the substituent on the nitrogen atom is methyl or phenylsulfonyl, furan and thiophene, or represents a bicyclic aromatic moiety selected from the group consisting of naphthalene, indole and benzothiophene, wherein Ar I may be substituted by one or more substituents selected from the group consisting of a halogen atom, a five- or six-membered aromatic heterocycle containing N, S or O, a $C_{1-6}$ aliphatic group and a $C_{3-6}$ cycloaliphatic group, wherein the $C_{1-6}$ aliphatic group and/or the $C_{3-6}$ cycloaliphatic group may additionally contain one or more heteroatoms selected from N, S and O, Ar II and Ar III each independently represent a benzene group, a pyridine group, a pyrrole group, a N-substituted pyrrole group wherein the substituent on the nitrogen atom is methyl or phenylsulfonyl or a thiophene group;

$R^1$ represents an aromatic group, a hydroxy group, a $C_1$-$C_6$ alkyl group or a $C_1$-$C_6$ alkoxy group; and X is selected from the group consisting of sugars, albumins, halogen atoms, $CH_3$, $NO_3$, CN, and $SR^5$, wherein $R^3$ is selected from the group consisting of 2,3,4,6-tetra-O-acetyl-β-D-glucopyranosyl, β-D-glucopyranosyl, 2,3,4,6-tetramesyl-β-D-gluco-pyranosyl, 2,3,4,6-tetra-O-acetyl-α-D-glucopyranosyl, 2,3,4,6-tetra-O-acetyl-β-D-galacto-pyranosyl, hepto-O-acetyl-β-maltosyl, 1,2-O-isopropylidene-5-α-D-xylo-furanosyl, $C_1$-$C_8$ alkyl, $CH(CO_2H)CH_2CO_2H$, 2-morpholinoethyl, 2'-ethyl-1-β-D-glucopyranosyl, 2'-ethyl-1-thio-β-D-glucopyranosyl, glutathionyl hydrochloride, CN, C(NH2)2·HCl, C(NH2)NHNH2, phenyl, 1-aminophenyl, 2-pyridyl, 6-methyl-2-pyridyl, 4-pyridyl, thiazoline-2-yl, 4,5-dihydrothiazol-2-yl, 1H-benzimidazol-2-yl, benzoxazol-2-yl, benzothiazol-2-yl, $(CH_2CH_2OH)_2NO_3$, pyrimidin-2-yl, 4-methylpyrimidin-2-yl, 4,6-dimehylpyrimidin-2-yl, 1,2-dihydropyridin-2-yl, 1,2-dihydropyrimidin-2-yl, 9H-purin-6-yl, 2-amino-9H-purin-6-yl, and $(NH_2)_2C$=; or a compound of Formula (B), (B)

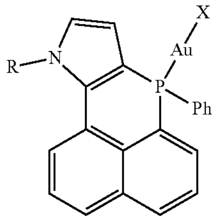

wherein R is methyl or $SO_2Ph$, and wherein X is chloride or 3,4,5-triacetyloxy-6-(acetyloxymethyl) oxane-2-thiolate;

and at least one pharmaceutically acceptable excipient.

16. The pharmaceutical composition according to claim 15, wherein the compound is dissolved in an aqueous solution comprising DMSO.

17. A method of treating brain cancer, or head and neck cancer in a subject in need thereof, comprising administering to the subject a therapeutically effective amount of the pharmaceutical composition according to claim 15.

18. The method according to claim 17, wherein the brain cancer is selected from glioblastoma, brain metastasis, meningioma, or IDH-mutant glioma.

19. The method according to claim 18, wherein the compound is administered intravenously.

20. A kit comprising at least a compound of Formula (A), (A)

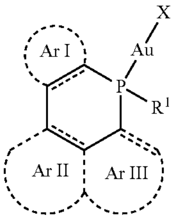

wherein

Ar I represents a monocyclic aromatic moiety selected from the group consisting of phenyl, pyridine, pyrrole, N-substituted pyrrole, wherein the substituent on the nitrogen atom is methyl or phenylsulfonyl, furan and thiophene, or represents a bicyclic aromatic moiety selected from the group consisting of naphthalene, indole and benzothiophene, wherein Ar I may be substituted by one or more substituents selected from the group consisting of a halogen atom, a five- or six-membered aromatic heterocycle containing N, S or O, a $C_{1-6}$ aliphatic group and a $C_{3-6}$ cycloaliphatic group, wherein the $C_{1-6}$ aliphatic group and/or the $C_{3-6}$ cycloaliphatic group may additionally contain one or more heteroatoms selected from N, S and O, Ar II and Ar III each independently represent a benzene group, a pyridine group, a pyrrole group, a N-substituted pyrrole group wherein the substituent on the nitrogen atom is methyl or phenylsulfonyl or a thiophene group;

$R^1$ represents an aromatic group, a hydroxy group, a $C_1$-$C_6$ alkyl group or a $C_1$-$C_6$ alkoxy group; and X is selected from the group consisting of sugars, albumins, halogen atoms, $CH_3$, $NO_3$, CN, and $SR^3$, wherein $R^3$ is selected from the group consisting of 2,3,4,6-tetra-O-acetyl-β-D-glucopyranosyl, β-D-glucopyranosyl, 2,3,4,6-tetramesyl-β-D-gluco-pyranosyl, 2,3,4,6-tetra-O-acetyl-α-D-glucopyranosyl, 2,3,4,6-tetra-O-acetyl-β-D-galacto-pyranosyl, hepto-O-acetyl-β-maltosyl, 1,2-O-isopropylidene-5-α-D-xylo-furanosyl, $C_1$-$C_8$ alkyl, $CH(CO_2H)CH_2CO_2H$, 2-morpholinoethyl, 2'-ethyl-1-β-D-glucopyranosyl, 2'-ethyl-1-thio-β-D-glucopyranosyl, glutathionyl hydrochloride, CN, C(NH2)2·HCl, C(NH2)NHNH2, phenyl, 1-aminophenyl, 2-pyridyl, 6-methyl-2-pyridyl, 4-pyridyl, thiazoline-2-yl, 4,5-dihydrothiazol-2-yl, 1H-benzimidazol-2-yl, benzoxazol-2-yl, benzothiazol-2-yl, $(CH_2CH_2OH)_2NO_3$, pyrimidin-2-yl, 4-methylpyrimidin-2-yl, 4,6-dimehylpyrimidin-2-yl, 1,2-dihydropyridin-2-yl, 1,2-dihydropyrimidin-2-yl, 9H-purin-6-yl, 2-amino-9H-purin-6-yl, and $(NH_2)_2C$=, or a compound of Formula (B), (B)

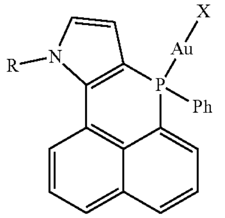

wherein R is methyl or $SO_2Ph$, and wherein X is chloride or 3,4,5-triacetyloxy-6-(acetyloxymethyl) oxane-2-thiolate, and a container.

21. The method according to claim 14, wherein the glioblastoma comprises glioblastoma stem-like cells.

* * * * *